US011192860B2

(12) United States Patent
Lengauer et al.

(10) Patent No.: US 11,192,860 B2
(45) Date of Patent: Dec. 7, 2021

(54) CO-CRYSTAL OF AN ORALLY AVAILABLE HIF PROLYL HYDROXYLASE INHIBITOR

(71) Applicant: Sandoz AG, Basel (CH)

(72) Inventors: Hannes Lengauer, Kundl (AT); Arthur Pichler, Kundl (AT); Renate Margreiter, Kundl (AT); Thomas Gelbrich, Innsbruck (AT)

( * ) Notice: Subject to any disclaimer, the term of this patent is extended or adjusted under 35 U.S.C. 154(b) by 0 days.

(21) Appl. No.: 16/643,886

(22) PCT Filed: Jul. 11, 2018

(86) PCT No.: PCT/EP2018/068754
§ 371 (c)(1),
(2) Date: Mar. 3, 2020

(87) PCT Pub. No.: WO2019/042641
PCT Pub. Date: Mar. 7, 2019

(65) Prior Publication Data
US 2020/0262792 A1    Aug. 20, 2020

(30) Foreign Application Priority Data

Sep. 4, 2017 (EP) ..................................... 17189195
Apr. 4, 2018 (EP) ..................................... 18165661

(51) Int. Cl.
*C07D 217/26* (2006.01)
*A61K 9/00* (2006.01)
*A61K 47/02* (2006.01)
*C07D 207/16* (2006.01)

(52) U.S. Cl.
CPC .......... *C07D 217/26* (2013.01); *A61K 9/0053* (2013.01); *A61K 47/02* (2013.01); *C07D 207/16* (2013.01); *C07B 2200/13* (2013.01)

(58) Field of Classification Search
CPC .................................................. C07D 217/26
USPC ........................................ 546/141; 514/309
See application file for complete search history.

(56) References Cited

FOREIGN PATENT DOCUMENTS

| IN | 201741028591 A | 8/2017 | |
|---|---|---|---|
| WO | 2004108681 A1 | 12/2004 | |
| WO | 2014014835 A3 | 8/2014 | |
| WO | 2014197660 A1 | 12/2014 | |
| WO | WO-2019030711 A1 * | 2/2019 | ........... C07D 213/82 |

OTHER PUBLICATIONS

Halebian et al., Pharmaceutical Applications, etc., Pharmaceutical Sciences 58(8), 1969, 911-929.*
Dean "Analytical Chem . . . . " p. 10.24-10.26 (1995).*
Seddon "Pseudopolymorph . . . . . . " Crystal Growth & design v.4(6) p. 1087 (2004) (2 pages from internet).*
Ivanisevic et al., "Use of X-ray . . . " Pharm. Sci. Encycl. p. 1-42 (2010).*
Ivanisevic et al., "Uses of X-ray, etc.," Pharm. Form. Qual. 2011, pp. 30-33.*
Bhattacharya et al., "Thermoanalytical and Crystallographic Methods" in Brittain H. ed., 2nd ed. Informa Healthcare:NY 2009 p. 318-335.*
U.S. Pharmacopia #23, National Formulary #18, 1843-1844. (Year: 1995).*
Aakeroy, "Crystal Engineering, etc.," Acta Cryst. (1997) B53, 569-586.*
Sekhon BS, "Pharmaceutical co-cyrstals, etc." Ars Pharm., 50(2): 99-117 (2009).*
Kirk-Othmer Encyclopedia of Chemical Technology, 8, pp. 95-147 (2002).*
Stahly, "Diversity in Single-, etc.", Crystal Growth & Design, 7 (6), 2007, 1007-1026.*
Vippagunta et al., "Crystalline Solids", Advanced Drug Delivery Reviews 48 (2001) 3-26.*
Braga et al., "Making crystals from . . . . " J. Royal Soc. Chem. Commun. p. 3635-3645 (2005).*
Davidovich et al., "Detection of polymorphism . . . . " Am. Pharm. Rev. v.&(1) p. 10, 12, 14, 16, 100 (2004).*
Bernstein, "Polymorphism, etc.," p. 115-118, 272. (Year: 2002).*
Dunitz, "Crystal, etc.," CrystEngComm, 5(91), 506. (Year: 2003).*
Childs et al., "The Salt-Cocrystal, etc.," Molecular Pharmaceutics, 4(3), 323-338. (Year: 2007).*
Weyna et al., "Synthesis and, etc.," Crystal Growth & Design, 9(2), 1106-1123. (Year: 2009).*
Healy, Anne Marie, et al., Pharmaceutical solvates, hydrates and amorphous forms: A special emphasis on cocrystals. Advanced Drug Delivery Reviews, 2017, vol. 117, pp. 25-46.
International Search Report and Written Opinion for PCT/EP2018/068754, 11 pages, Oct. 2019.
Pecharsky and Zavalij, Fundamentals of Powder Diffraction and Structural Characterization of Materials, Springer, 2005, p. 3.
Shewale, Sheetal, et al., American Journal of PharmTech Research, 2015, pp. 90-107.
Takata, Noriyuki, Pharm Tech Japan, 2009, vol. 25, No. 12, pp. 155-166.
Tilborg, Anaelle, et al., European Journal of Medicinal Chemistry, 2014, vol. 74, pp. 411-426.

* cited by examiner

*Primary Examiner* — Patricia L Morris
(74) *Attorney, Agent, or Firm* — Luedeka Neely Group, P.C.

(57) ABSTRACT

The present invention relates to a co-crystal of roxadustat with L-proline and to a process for its preparation. Furthermore, the invention relates to a pharmaceutical composition comprising said roxadustat L-proline co-crystal, at least one pharmaceutically acceptable excipient and optionally at least one photostabilizing agent. The pharmaceutical composition of the present invention can be used as a medicament, in particular for the treatment and/or prevention of anemia in patients with end-stage renal disease (ESRD) and/or chronic kidney disease (CKD).

9 Claims, 12 Drawing Sheets

CO-CRYSTAL OF AN ORALLY AVAILABLE HIF PROLYL HYDROXYLASE INHIBITOR

This application is a Section 371 national phase entry of PCT application PCT/EP2018/068754, filed Jul. 11, 2018. This application also claims the benefit of the earlier filing dates of European patent application 17189195.5, filed Sep. 4, 2017 and of European patent application 18165661.2, filed Apr. 4, 2018.

FIELD OF THE INVENTION

The present invention relates to a co-crystal of roxadustat with L-proline and to a process for its preparation. Furthermore, the invention relates to a pharmaceutical composition comprising said roxadustat L-proline co-crystal, at least one pharmaceutically acceptable excipient and optionally at least one photostabilizing agent. The pharmaceutical composition of the present invention can be used as a medicament, in particular for the treatment and/or prevention of anemia in patients with end-stage renal disease (ESRD) and/or chronic kidney disease (CKD).

BACKGROUND OF THE INVENTION

Roxadustat is an orally available hypoxia inducible factor (HIF) prolyl hydroxylase inhibitor. HIF prolyl hydroxylase inhibitors are useful for increasing the stability and/or activity of HIF, and thus are useful for treating and preventing HIF associated disorders including anemia-, ischemia- and hypoxia-related disorders.

Roxadustat is chemically also designated [(4-hydroxy-1-methyl-7-phenoxyisoquinoline-3-carbonyl)amino]acetic acid and can be represented by the chemical structure as depicted in formula A:

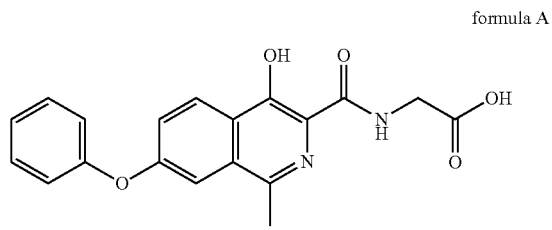 [SMILES: Cc1nc(C(=O)NCC(=O)O)c(O)c2ccc(Oc3ccccc3)cc12]

formula A

The compound roxadustat is disclosed in WO 2004/108681 A1. WO 2014/014835 A2 discloses beside amorphous roxadustat several crystalline forms of roxadustat such as an anhydrous form A, a hemihydrate form B, a hexafluoropropan-2-ol solvate form C and a mixed DMSO/water solvate form D. The same application also mentions several crystalline and amorphous salts of roxadustat such as salts with the alkali metals sodium and potassium, with the alkaline earth metals calcium and magnesium, with the amino acids L-arginine and L-lysine, with the amines ethanolamine, diethanolamine, tromethamine and triethylamine and with hydrochloric acid, sulfuric acid and methanesulfonic acid.

Different solid-state forms of an active pharmaceutical ingredient (API) often possess different physical and chemical properties such as but not limited to dissolution rate, solubility, chemical stability, physical stability, hygroscopicity, melting point, morphology, flowability, bulk density and compressibility. Apart from conventional solid-state forms of an API, such as polymorphs, pseudopolymorphs (hydrates and solvates) and salts, pharmaceutical co-crystals open up further opportunities for customizing the physicochemical properties of APIs with a process or clinical need. For example, they can be tailored to enhance drug product bioavailability and stability and to enhance the processability of APIs during drug product manufacture.

Co-crystals are structurally readily distinguishable from salts because unlike salts, their components are in a neutral state and interact nonionically. In addition, co-crystals structurally differ from polymorphs, which are defined as including only single-component crystalline forms that have different arrangements or conformations of the molecules in the crystal lattice Instead, co-crystals are structurally more similar to solvates and hydrates, in that both contain more than one component in the crystal lattice and the interaction between these components is nonionic. From a physical chemistry perspective, co-crystals can be viewed as a special case of solvates and hydrates, wherein the second component, the co-crystal former, is nonvolatile. (see also "Regulatory Classification of Pharmaceutical Co-Crystals", Guidance for Industry, FDA, Revision 1, August 2016).

The known hydrates and solvates of roxadustat, which are described in WO 2014/014835 A2 suffer from certain drawbacks e.g. they are physically unstable upon temperature stress and readily transform to the anhydrous form A of WO 2014/014835 A2 as indicated by the DSC curves provided in said application. This is critical, because the sudden appearance or disappearance of a solid-state form of an active pharmaceutical ingredient can pose a problem in process development. Similarly, serious pharmaceutical consequences can arise if transformation occurs in a dosage form. In addition, forms C and D contain significant amounts of organic solvents such as hexafluoropropan-2-ol solvate (form C) and DMSO (form D) which should be removed to the extent possible, since there is no therapeutic benefit from organic solvents.

It is thus an objective of the present invention to provide an improved solid-state form of roxadustat, in particular a co-crystal of roxadustat, which is physically stable against temperature stress. It is a further objective of the present invention to provide an improved solid-state form of roxadustat, in particular a co-crystal of roxadustat, which is chemically stable e.g. against photodegradation, essentially free of organic solvents, characterized by improved dissolution/solubility and/or characterized by improved powder characteristics such as flowability, bulk density and compressibility.

SUMMARY OF THE INVENTION

The invention solves one or more of the above defined objectives by providing a pharmaceutical co-crystal of roxadustat with L-proline. The co-crystal of the present invention possesses one or more improved physicochemical properties selected from dissolution rate, solubility, chemical stability, physical stability, hygroscopicity, melting point, morphology, flowability, bulk density and compressibility. In particular, the co-crystal of the present invention is thermally more stable compared to the hemihydrate form B and the solvates form C and D of WO 2014/014835 A2, which all desolvate/dehydrate upon heating and finally show at least a partial phase transformation to the anhydrous form A of roxadustat.

Abbreviations

PXRD powder X-ray diffractogram
SXRD single X-ray diffraction

FTIR Fourier transform infrared
ATR attenuated total reflection
DSC differential scanning calorimetry
TGA thermogravimetric analysis
NMR nuclear magnetic resonance
RT room temperature
RH relative humidity
API active pharmaceutical ingredient
THF tetrahydrofuran Definitions As used herein the term "room temperature" refers to a temperature in the range of from 20 to 30° C.

The term "roxadustat" as used herein refers to [(4-hydroxy-1-methyl-7-phenoxyisoquinoline-3-carbonyl)amino] acetic acid according to the chemical structure depicted in formula A disclosed herein above.

The term "co-crystal" as used herein refers to crystalline materials composed of two or more different molecular and/or ionic compounds in the same crystal lattice that are associated by nonionic and noncovalent bonds, wherein at least two of the individual molecular and/or ionic compounds are solids at room temperature.

The terms "roxadustat co-crystal with L-proline" or "co-crystal of roxadostat with L-proline" or "roxadustat L-proline co-crystal" as used interchangeably herein refer to a crystalline compound comprising roxadustat as active pharmaceutical ingredient and L-proline, preferably present as zwitterion, as co-crystal former in the same crystal lattice, wherein the interaction between roxadustat and L-proline is of nonionic and noncovalent nature.

The term "zwitterion" as used herein describes a neutral molecule with both positive and negative electrical charges. Zwitterions are sometimes called "inner salts".

The term "roxadustat form A" as used herein, refers to the crystalline form of roxadustat, which is disclosed in WO 2014/014835 A2. Form A of roxadustat can be characterized by having a powder X-ray diffractogram comprising reflections at 2-Theta angles of (8.5±0.2°), (16.2±0.2°) and (27.4±0.2°), when measured at a temperature in the range of from 20 to 30° C. with Cu-Kalpha$_{1,2}$ radiation having a wavelength of 0.15419 nm.

As used herein, the term "measured at a temperature in the range of from 20 to 30° C." refers to a measurement under standard conditions. Typically, standard conditions mean a temperature in the range of from 20 to 30° C., i.e. at room temperature. Standard conditions can mean a temperature of about 22° C. Typically, standard conditions can additionally mean a measurement under 20-50% relative humidity.

The term "reflection" with regard to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see *"Fundamentals of Powder Diffraction and Structural Characterization of Materials"* by Vitalij K. Pecharsky and Peter Y. Zavalij, Kluwer Academic Publishers, 2003, page 3).

The term "essentially the same" with reference to powder X-ray diffraction means that variabilities in reflection positions and relative intensities of the reflections are to be taken into account. For example, a typical precision of the 2-Theta values is in the range of ±0.2° 2-Theta, preferably in the range of ±0.1° 2-Theta. Thus, a reflection that usually appears at 3.6° 2-Theta for example can appear between 3.4° and 3.8° 2-Theta, preferably between 3.5 and 3.7° 2-Theta on most X-ray diffractometers under standard conditions. Furthermore, one skilled in the art will appreciate that relative reflection intensities will show inter-apparatus variability as well as variability due to degree of crystallinity, preferred orientation, sample preparation and other factors known to those skilled in the art and should be taken as qualitative measure only.

The term "essentially the same" with reference to Fourier transform infrared spectroscopy means that variabilities in peak positions and relative intensities of the peaks are to be taken into account. For example, a typical precision of the wavenumber values is in the range of ±2 cm$^{-1}$. Thus, a peak at 3379 cm$^{-1}$ for example can appear in the range of from 3381 to 3377 cm$^{-1}$ on most infrared spectrometers under standard conditions. Differences in relative intensities are typically smaller compared to X-ray diffraction. However, one skilled in the art will appreciate that small differences in peak intensities due to degree of crystallinity, sample preparation and other factors can also occur in infrared spectroscopy. Relative peak intensities should therefore be taken as qualitative measure only.

The term "essentially the same" with reference to Raman spectroscopy means that variabilities in peak positions and relative intensities of the peaks are to be taken into account. For example, a typical precision of the wavenumber values is in the range of ±3 cm$^{-1}$. Thus, a peak at 1629 cm$^{-1}$ for example can appear in the range of from 1626 to 1632 cm$^{-1}$ on most Raman spectrometers under standard conditions. Differences in relative intensities are typically smaller compared to X-ray diffraction. However, one skilled in the art will appreciate that small differences in peak intensities due to degree of crystallinity, sample preparation and other factors can also occur in Raman spectroscopy. Relative peak intensities should therefore be taken as qualitative measure only.

The term "solid-state form" as used herein refers to any crystalline and/or amorphous phase of a compound. Crystalline phases include anhydrous/non-solvated forms of a compound and their polymorphs, hydrates and solvates of a compound and their polymorphs, salts and co-crystals of a compound and any mixtures thereof.

As used herein, the term "essentially free of any other solid-state form" with reference to the composition comprising the roxadustat L-proline co-crystal of the present invention, means that the roxadustat L-proline co-crystal contains at most 20 weight %, preferably at most 10 weight %, more preferably at most 5 weight %, 4 weight %, 3 weight %, 2 weight % or 1 weight % of any other solid-state form of roxadustat, in particular roxadustat form A, based on the weight of the composition.

The terms "anhydrous" or "anhydrate" as used herein refer to a crystalline solid where no water is cooperated in or accommodated by the crystal structure. Anhydrous forms may still contain residual water, which is not part of the crystal structure but may be adsorbed on the surface or absorbed in disordered regions of the crystal. Typically, an anhydrous form does not contain more than 1.0 weight %, preferably not more than 0.5 weight % and most preferably not more than 0.3 weight %, 0.2 weight % or 0.1 weight % of water, based on the weight of the crystalline form. The water content can be determined by Karl-Fischer Coulometry and/or by thermogravimetric analysis (TGA), e.g. by determining the mass loss in the range of from 25 to 180° C., 190° C. or 200° C. at a heating rate of 10 K/min.

The term "non-solvated" as used herein, when talking about a crystalline solid indicates that no organic solvent is cooperated in or accommodated by the crystal structure. Non-solvated forms may still contain residual organic solvents, which are not part of the crystal structure but may be adsorbed on the surface or absorbed in disordered regions of the crystal. Typically, a non-solvated form does not contain more than 1.0 weight %, preferably not more than 0.5 weight %, and most preferably not more than 0.3 weight %, 0.2 weight % or 0.1 weight % of organic solvents, based on the weight of the crystalline form. The organic solvent content can be determined by thermogravimetric analysis (TGA), e.g. by determining the mass loss in the range of from 25 to 180° C., 190° C. or 200° C. at a heating rate of 10 K/min or by $^1$H-NMR.

The roxadustat L-proline co-crystal may be referred to herein as being characterized by a powder X-ray diffractogram, a Fourier transform infrared spectrum and/or a Raman spectrum "as shown in" a figure. The person skilled in the art understands that factors such as variations in instrument type, response and variations in sample directionality, sample concentration, sample purity, sample history and sample preparation may lead to variations, for example relating to the exact reflection or peak positions and intensities. However, a comparison of the graphical data in the figures herein with the graphical data generated for an unknown physical form and the confirmation that two sets of graphical data relate to the same crystal form is well within the knowledge of a person skilled in the art.

As used herein, the term "mother liquor" refers to the solution remaining after crystallization of a solid from said solution.

A "predetermined amount" as used herein with regard to roxadustat L-proline co-crystal of the present invention refers to the initial amount of the roxadustat L-proline co-crystal used for the preparation of a pharmaceutical composition having a desired dosage strength of roxadustat.

As used herein, the term "effective amount" in conjunction with the roxadustat L-proline co-crystal of the present invention encompasses an amount of the the roxadustat L-proline co-crystal which causes the desired therapeutic or prophylactic effect.

As used herein, the term "about" means within a statistically meaningful range of a value. Such a range can be within an order of magnitude, typically within 10%, more typically within 5%, even more typically within 1% and most typically within 0.1% of the indicated value or range. Sometimes, such a range can lie within the experimental error, typical of standard methods used for the measurement and/or determination of a given value or range.

The term "pharmaceutically acceptable excipient" as used herein refers to substances, which do not show a significant pharmacological activity at the given dose and that are added to a pharmaceutical composition in addition to the active pharmaceutical ingredient. Excipients may take the function of vehicle, diluent, release agent, disintegrating agent, dissolution modifying agent, absorption enhancer, stabilizer or a manufacturing aid among others. Excipients may include fillers (diluents), binders, disintegrants, lubricants and glidants.

The terms "filler" or "diluent" as used herein refer to substances that are used to dilute the active pharmaceutical ingredient prior to delivery. Diluents and fillers can also serve as stabilizers.

As used herein the term "binder" refers to substances which bind the active pharmaceutical ingredient and pharmaceutically acceptable excipient together to maintain cohesive and discrete portions.

The terms "disintegrant" or "disintegrating agent" as used herein refers to substances which, upon addition to a solid pharmaceutical composition, facilitate its break-up or disintegration after administration and permits the release of the active pharmaceutical ingredient as efficiently as possible to allow for its rapid dissolution.

The term "lubricant" as used herein refers to substances which are added to a powder blend to prevent the compacted powder mass from sticking to the equipment during tableting or encapsulation process. They aid the ejection of the tablet from the dies and can improve powder flow.

The term "glidant" as used herein refers to substances which are used for tablet and capsule formulations in order to improve flow properties during tablet compression and to produce an anti-caking effect.

The term "photostabilizing agent" as used herein refers to substances which prevent or reduce the photodegradation or photodecomposition of the active pharmaceutical ingredient upon light exposure. In other words, the photostabilizing agent functions to prevent or reduce the formation of photodegradation products. Typically, the photostabilizing agent prevents or reduces the photodegradation of the light sensitive active pharmaceutical ingredient by blocking or reducing the exposure of the molecule to light within a wavelength range.

As used herein, the term "effective amount" in conjunction with a photostabilizing agent encompasses an amount of the photostabilizing agent which is sufficient to prevent or reduce the photodegradation of the active pharmaceutical ingredient, such that the amount of photodegradation products that is produced is limited to a desired maximum level under specific light conditions.

DETAILED DESCRIPTION OF THE INVENTION

Figure 1:
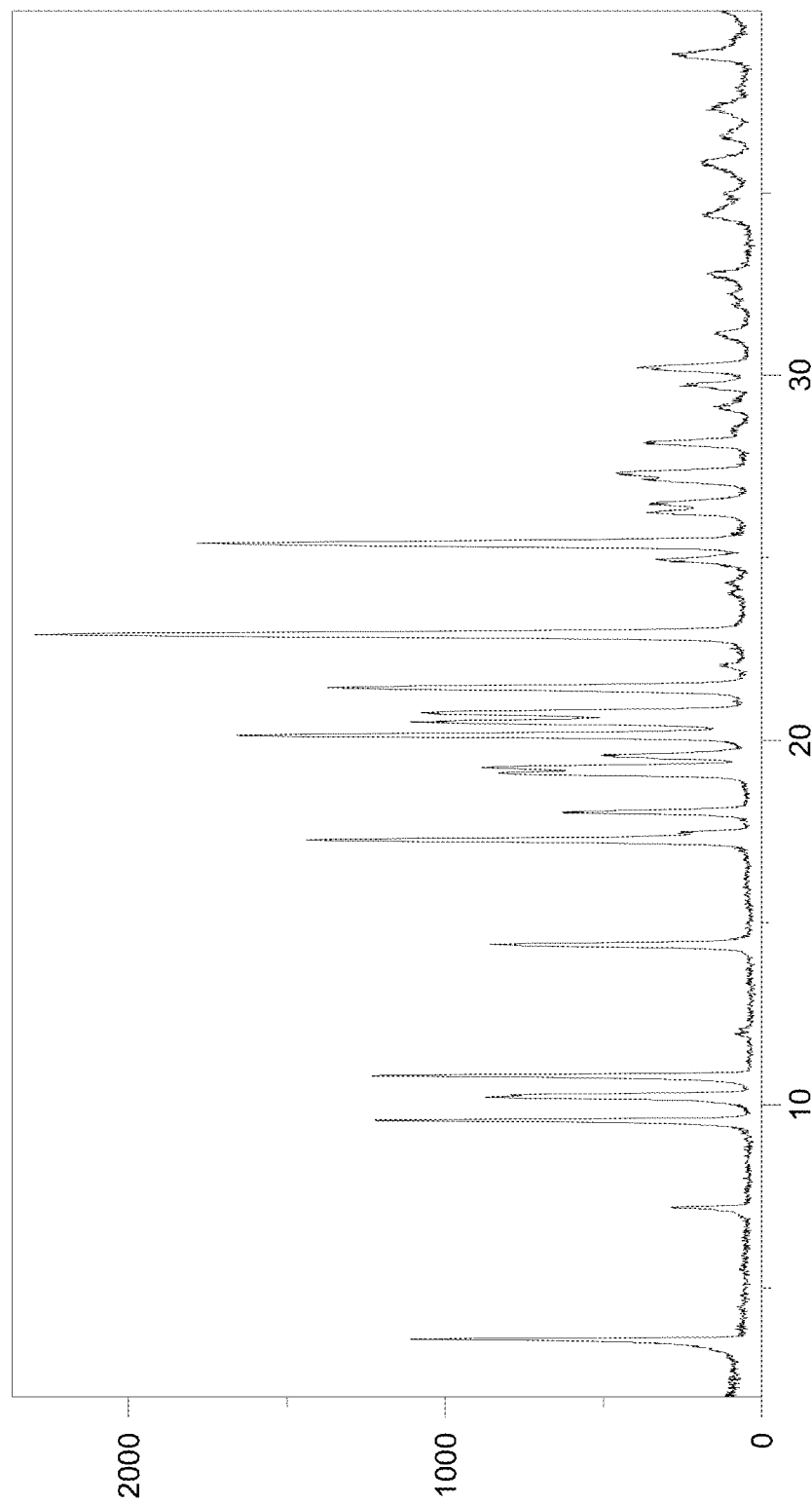
FIG. 1: illustrates a representative PXRD of the roxadustat L-proline co-crystal according to the present invention. The x-axis shows the scattering angle in ° 2-Theta, the y-axis shows the intensity of the scattered X-ray beam in counts of detected photons.

The present invention provides a pharmaceutical co-crystal composed of roxadustat as the active pharmaceutical ingredient and L-proline, preferably present as zwitterion, as the co-crystal former.

The roxadustat L-proline co-crystal of the present invention is physically stable toward temperature stress e.g. it shows no thermal events in a DSC experiment until it starts to melt at about 206° C. Moreover, a TGA experiment performed with the co-crystal of the present invention revealed no significant mass loss until melting, which indicates the presence of an anhydrous and non-solvated solid-state form, which was finally proved by SXRD. In addition, the roxadustat L-proline co-crystal of the present invention shows advantageous dissolution behavioiur, good chemical stability e.g. against photodegradation and is characterized by excellent powder properties such as good flowability, high bulk density and good compressibility. All in all, these favorable attributes allow for a robust formulation and ensure a reliable safety and efficacy profile of a drug product containing the roxadustat L-proline co-crystal of the present invention during the whole shelf-life of the product.

The roxadustat L-proline co-crystal of the present invention may be characterized by analytical methods well known in the field of the pharmaceutical industry for characterizing crystalline solids. Such methods comprise but are not limited to powder and single X-ray diffraction, Fourier transform and Raman spectroscopy, DSC, TGA and GMS. The co-crystal of the present invention may be characterized by one of the aforementioned analytical methods or by combining two or more of them. In particular, the co-crystal of the present invention may be characterized by any one of the following embodiments or by combining two or more of the following embodiments.

In a first aspect, the invention relates to a co-crystal of roxadustat with L-proline.

In one embodiment, the invention relates to a co-crystal of roxadustat with L-proline characterized by having the chemical structure as depicted in formula B1

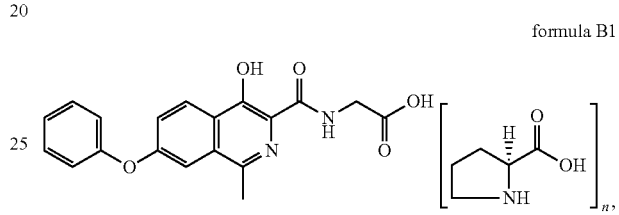

formula B1 wherein n is in the range of from 0.8 to 1.2, preferably of from 0.9 to 1.1, even more preferably of from 0.95 to 1.05 and most preferably n is 1.0.

In another embodiment, the invention relates to a co-crystal of roxadustat with L-proline characterized by having the chemical structure as depicted in formula B2

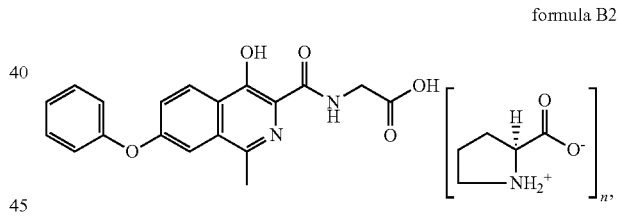

formula B2 wherein n is in the range of from 0.8 to 1.2, preferably of from 0.9 to 1.1, even more preferably of from 0.95 to 1.05 and most preferably n is 1.0.

In another embodiment the invention relates to a co-crystal of roxadustat with L-proline characterized by having a PXRD comprising reflections at 2-Theta angles of:
(3.6±0.2°), (7.2±0.2°) and (9.6±0.2°); or
(3.6±0.2°), (7.2±0.2°), (9.6±0.2°) and (10.8±0.2°); or
(3.6±0.2°), (7.2±0.2°), (9.6±0.2°), (10.8±0.2°) and (14.4±0.2°); or
(3.6±0.2°), (7.2±0.2°), (9.6±0.2°), (10.8±0.2°), (14.4±0.2°) and (17.3±0.2°); or
(3.6±0.2°), (7.2±0.2°), (9.6±0.2°), (10.8±0.2°), (14.4±0.2°), (17.3±0.2°) and (21.4±0.2°); or
(3.6±0.2°), (7.2±0.2°), (9.6±0.2°), (10.8±0.2°), (14.4±0.2°), (17.3±0.2°), (21.4±0.2°) and (22.9±0.2°); or
(3.6±0.2°), (7.2±0.2°), (9.6±0.2°), (10.8±0.2°), (14.4±0.2°), (17.3±0.2°), (21.4±0.2°), (22.9±0.2°) and (25.4±0.2°); or
(3.6±0.2°), (7.2±0.2°), (9.6±0.2°), (10.2±0.2°), (10.8±0.2°), (14.4±0.2°), (17.3±0.2°), (21.4±0.2°), (22.9±0.2°) and (25.4±0.2°), when measured at RT with Cu-Kalpha$_{1,2}$ radiation having a wavelength of 0.15419 nm.

In a further embodiment the invention relates to a co-crystal of roxadustat with L-proline characterized by having a PXRD comprising reflections at 2-Theta angles of:
(3.6±0.1°), (7.2±0.1°) and (9.6±0.1°); or
(3.6±0.1°), (7.2±0.1°), (9.6±0.1°) and (10.8±0.1°); or
(3.6±0.1°), (7.2±0.1°), (9.6±0.1°), (10.8±0.1°) and (14.4±0.1°); or
(3.6±0.1°), (7.2±0.1°), (9.6±0.1°), (10.8±0.1°), (14.4±0.1°) and (17.3±0.1°); or
(3.6±0.1°), (7.2±0.1°), (9.6±0.1°), (10.8±0.1°), (14.4±0.1°), (17.3±0.1°) and (21.4±0.1°); or
(3.6±0.1°), (7.2±0.1°), (9.6±0.1°), (10.8±0.1°), (14.4±0.1°), (17.3±0.1°), (21.4±0.1°) and (22.9±0.1°); or
(3.6±0.1°), (7.2±0.1°), (9.6±0.1°), (10.8±0.1°), (14.4±0.1°), (17.3±0.1°), (21.4±0.1°), (22.9±0.1°) and (25.4±0.1°); or
(3.6±0.1°), (7.2±0.1°), (9.6±0.1°), (10.2±0.1°), (10.8±0.1°), (14.4±0.1°), (17.3±0.1°),
(21.4±0.1°), (22.9±0.1°) and (25.4±0.1°),
when measured at a temperature in the range of from 20 to 30° C. with Cu-Kalpha$_{1,2}$ radiation having a wavelength of 0.15419 nm.

In yet another embodiment the invention relates to a co-crystal of roxadustat with L-proline, characterized by having a PXRD essentially the same as shown in FIG. 1 of the present invention, when measured at RT with Cu-Kalpha$_{1,2}$ radiation having a wavelength of 0.15419 nm.

In a further embodiment, the present invention relates to a co-crystal of roxadustat with L-proline, characterized by having a FTIR spectrum comprising peaks at wavenumbers of:
(3379±2) cm$^{-1}$, (3071±2) cm$^{-1}$ and (1705±2) cm$^{-1}$ or;
(3379±2) cm$^{-1}$, (3071±2) cm$^{-1}$, (1705±2) cm$^{-1}$ and (1624±2) cm$^{-1}$; or
(3379±2) cm$^{-1}$, (3071±2) cm$^{-1}$, (1705±2) cm$^{-1}$, (1624±2) cm$^{-1}$ and (1529±2) cm$^{-1}$; or
(3379±2) cm$^{-1}$, (3071±2) cm$^{-1}$, (1705±2) cm$^{-1}$, (1624±2) cm$^{-1}$, (1529±2) cm$^{-1}$ and (1487±2) cm$^{-1}$; or
(3379±2) cm$^{-1}$, (3071±2) cm$^{-1}$, (1705±2) cm$^{-1}$, (1624±2) cm$^{-1}$, (1529±2) cm$^{-1}$, (1487±2) cm$^{-1}$ and (1408±2) cm$^{-1}$; or
(3379±2) cm$^{-1}$, (3071±2) cm$^{-1}$, (1705±2) cm$^{-1}$, (1624±2) cm$^{-1}$, (1529±2) cm$^{-1}$, (1487±2) cm$^{-1}$, (1408±2) cm$^{-1}$ and (1332±2) cm$^{-1}$; or
(3379±2) cm$^{-1}$, (3071±2) cm$^{-1}$, (1705±2) cm$^{-1}$, (1624±2) cm$^{-1}$, (1529±2) cm$^{-1}$, (1487±2) cm$^{-1}$, (1408±2) cm$^{-1}$, (1332±2) cm$^{-1}$ and (1244±2) cm$^{-1}$; or
(3379±2) cm$^{-1}$, (3071±2) cm$^{-1}$, (1705±2) cm$^{-1}$, (1624±2) cm$^{-1}$, (1529±2) cm$^{-1}$, (1487±2) cm$^{-1}$, (1408±2) cm$^{-1}$, (1332±2) cm$^{-1}$, (1244±2) cm$^{-1}$ and (1203±2) cm$^{-1}$,
when measured at RT with a diamond ATR cell.

Figure 2:
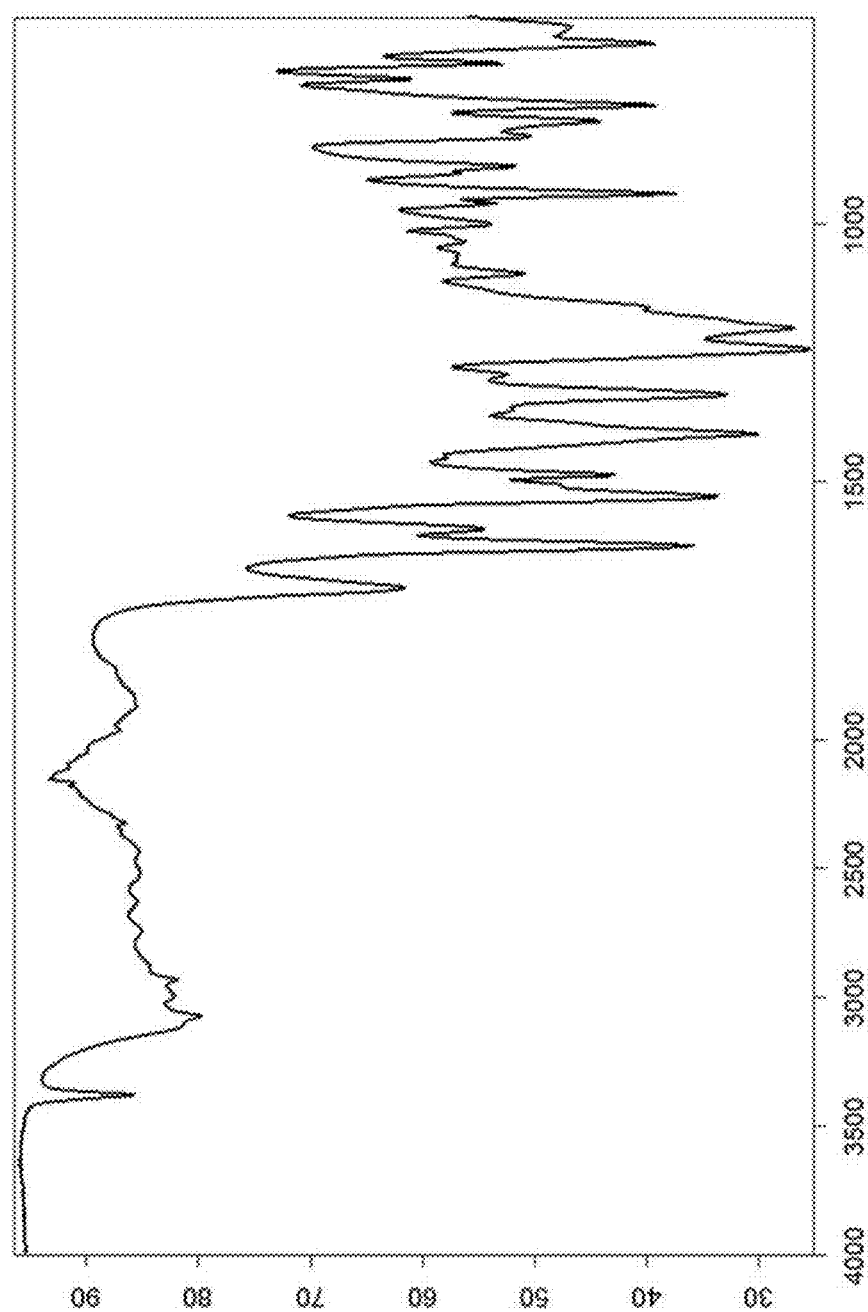
FIG. 2: illustrates a representative FTIR spectrum of the roxadustat L-proline co-crystal according to the present invention. The x-axis shows the wavenumbers in cm$^{-1}$, the y-axis shows the relative intensity in percent transmittance.

In yet another embodiment, the present invention relates to a co-crystal of roxadustat with L-proline, characterized by having a FTIR spectrum essentially the same as shown in FIG. 2 of the present invention, when measured at RT with a diamond ATR cell.

In a further embodiment, the present invention relates to a co-crystal of roxadustat with L-proline, characterized by having a Raman spectrum comprising peaks at wavenumbers of:
(1629±3) cm$^{-1}$, (1536±3) cm$^{-1}$ and (1412±3) cm$^{-1}$; or
(1629±3) cm$^{-1}$, (1583±3) cm$^{-1}$, (1536±3) cm$^{-1}$ and (1412±3) cm$^{-1}$; or
(1629±3) cm$^{-1}$, (1583±3) cm$^{-1}$, (1536±3) cm$^{-1}$, (1412±3) cm$^{-1}$ and (1366±3) cm$^{-1}$; or
(1629±3) cm$^{-1}$, (1583±3) cm$^{-1}$, (1536±3) cm$^{-1}$, (1412±3) cm$^{-1}$, (1366±3) cm$^{-1}$ and (1296±3) cm$^{-1}$; or
(1629±3) cm$^{-1}$, (1583±3) cm$^{-1}$, (1536±3) cm$^{-1}$, (1412±3) cm$^{-1}$, (1366±3) cm$^{-1}$, (1296±3) cm$^{-1}$ and (1186±3) cm$^{-1}$; or
(1629±3) cm$^{-1}$, (1583±3) cm$^{-1}$, (1536±3) cm$^{-1}$, (1412±3) cm$^{-1}$, (1366±3) cm$^{-1}$, (1296±3) cm$^{-1}$, (1186±3) cm$^{-1}$ and (1003±3) cm$^{-1}$; or
(1629±3) cm$^{-1}$, (1583±3) cm$^{-1}$, (1536±3) cm$^{-1}$, (1412±3) cm$^{-1}$, (1366±3) cm$^{-1}$, (1296±3) cm$^{-1}$, (1186±3) cm$^{-1}$, (1003±3) cm$^{-1}$ and (821±3) cm$^{-1}$; or
(1629±3) cm$^{-1}$, (1583±3) cm$^{-1}$, (1536±3) cm$^{-1}$, (1412±3) cm$^{-1}$, (1366±3) cm$^{-1}$, (1296±3) cm$^{-1}$, (1186±3) cm$^{-1}$, (1003±3) cm$^{-1}$, (821±3) cm$^{-1}$ and (518±3) cm$^{-1}$,
when measured at RT and a wavelength of 785 nm.

Figure 3:
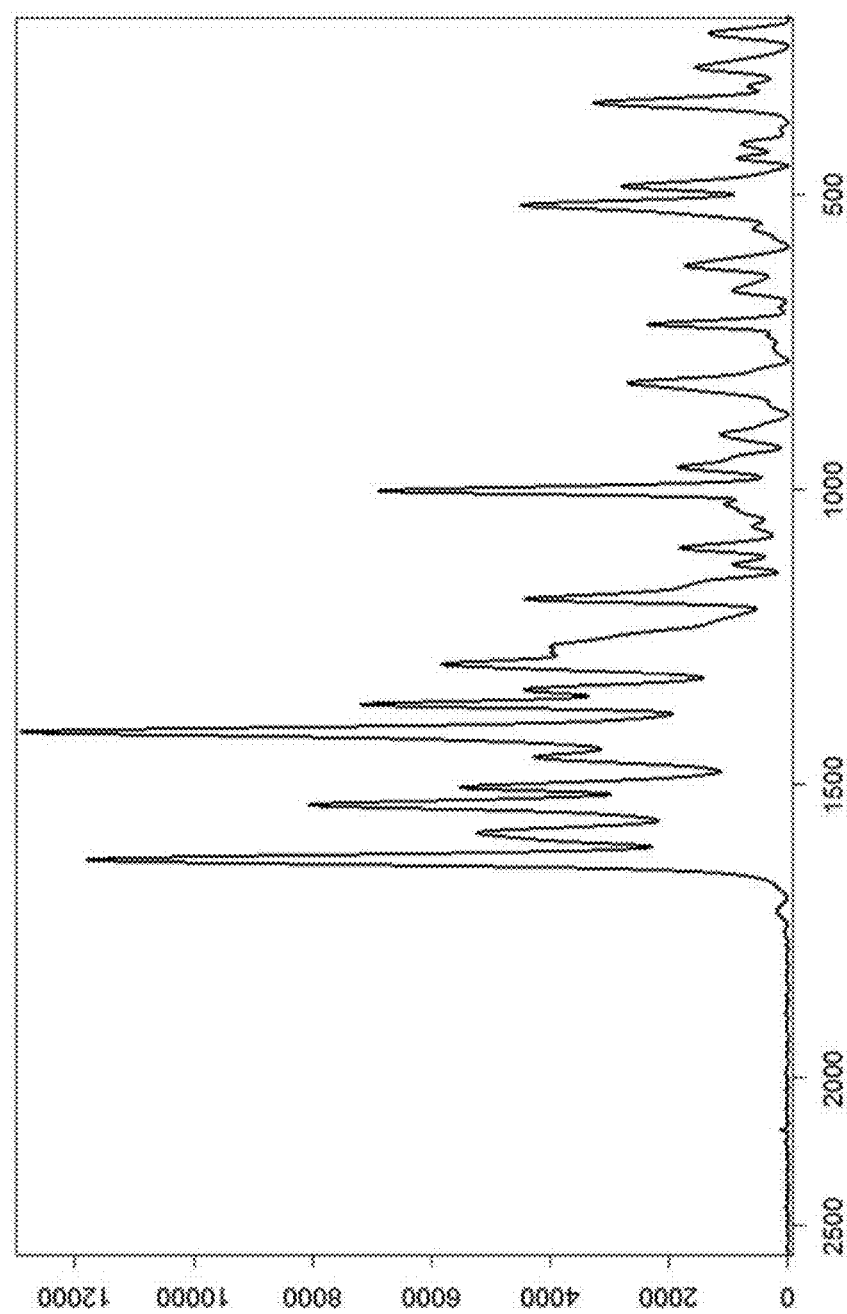
FIG. 3: illustrates a representative Raman spectrum of the roxadustat L-proline co-crystal according to the present invention. The x-axis shows the wavenumbers in cm$^{-1}$, the y-axis shows the Raman intensity.

In yet another embodiment, the present invention relates to a co-crystal of roxadustat with L-proline, characterized by having a Raman spectrum essentially the same as shown in FIG. 3 of the present invention, when measured at RT and a wavelength of 785 nm.

In a further embodiment, the present invention relates to a co-crystal of roxadustat with L-proline characterized by exhibiting monoclinic unit cells having space group P2$_1$ with the following parameters:
a=9.1583
b=4.9686
c=24.655
alpha=90°
beta=90.415°
gamma=90°
when measured with single crystal X-ray diffraction at (173±2) K with Mo-Kalpha$_{1,2}$ radiation having a wavelength of 0.71073 Angstrom.

In one embodiment, the present invention relates to a co-crystal of roxadustat with L-proline characterized in that the co-crystal is anhydrous.

In another embodiment, the present invention relates to a co-crystal of roxadustat with L-proline characterized in that the co-crystal is non-solvated.

In another embodiment, the present invention relates to a co-crystal of roxadustat with L-proline, characterized by having a DSC curve comprising an endothermic peak, preferably a single endothermic peak, having an onset temperature of (206±1°) C., when measured with DSC at a heating rate of 10 K/min.

In a further embodiment, the present invention relates to a co-crystal of roxadustat with L-proline, characterized by having a DSC curve comprising an endothermic peak, preferably a single endothermic peak, having a peak temperature of (207±1°) C., when measured with DSC at a heating rate of 10 K/min.

In another embodiment, the present invention relates to a co-crystal of roxadustat with L-proline, characterized by having a TGA curve showing a mass loss of 0.5 weight % or less, preferably of 0.1 weight % or less based on the weight of the co-crystal, when heated from RT to 180° C. at a rate of 10 K/min.

In a further embodiment, the present invention relates to a co-crystal of roxadustat with L-proline, characterized by having a TGA curve showing a mass loss of 0.5 weight % or less, preferably of 0.2 weight % or less based on the weight of the co-crystal, when heated from RT to 190° C. at a rate of 10 K/min.

In yet a further embodiment, the present invention relates to a co-crystal of roxadustat with L-proline, characterized by having a TGA curve showing a mass loss of 0.5 weight % or less, preferably of 0.3 weight % or less based on the weight of the co-crystal, when heated from RT to 200° C. at a rate of 10 K/min.

Figure 4:
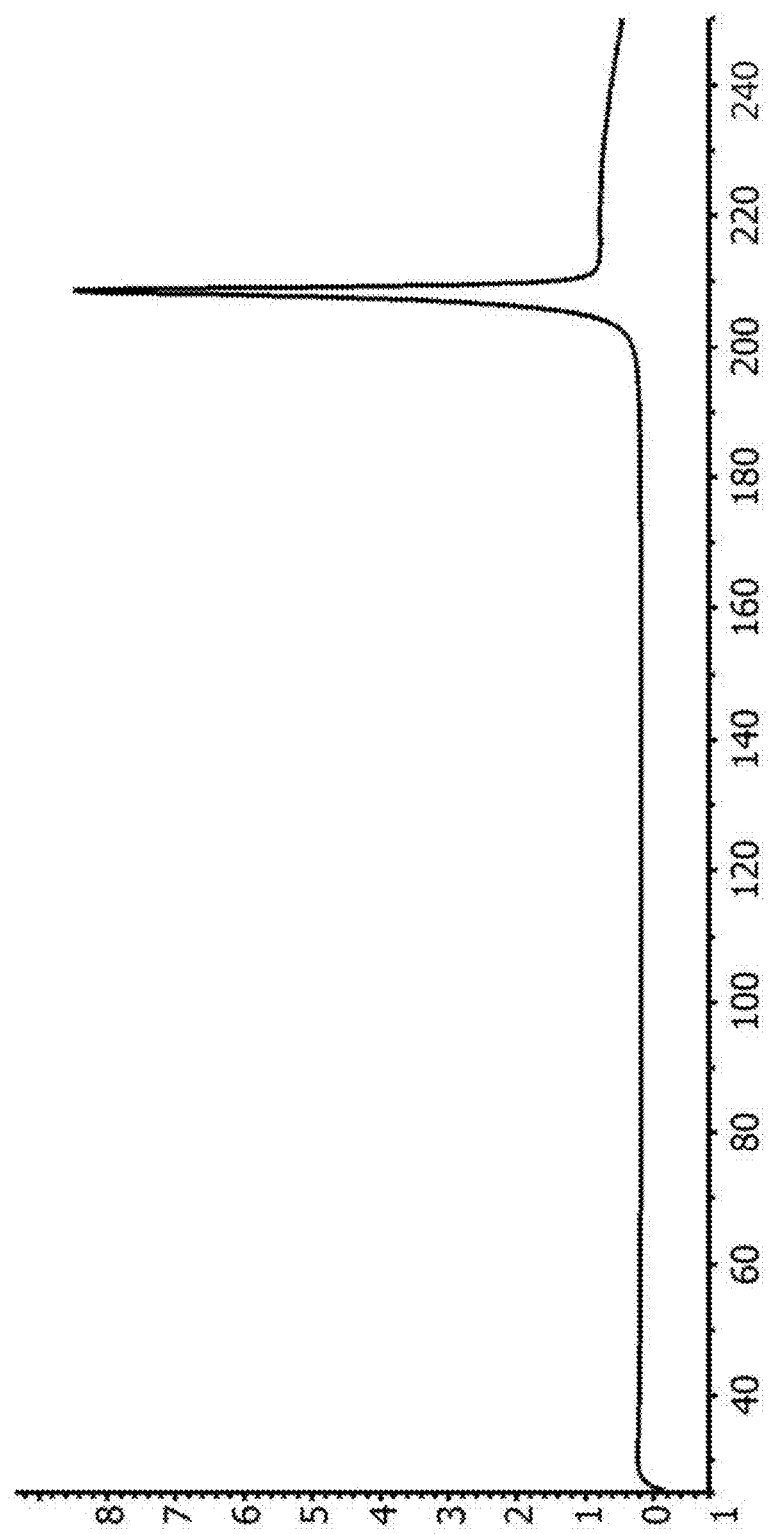
FIG. 4: illustrates a representative DSC curve of the roxadustat L-proline co-crystal according to the present invention. The x-axis shows the temperature in degree Celsius (° C.), the y-axis shows the heat flow rate in Watt per gram (W/g) with endothermic peaks going up.
Figure 5:
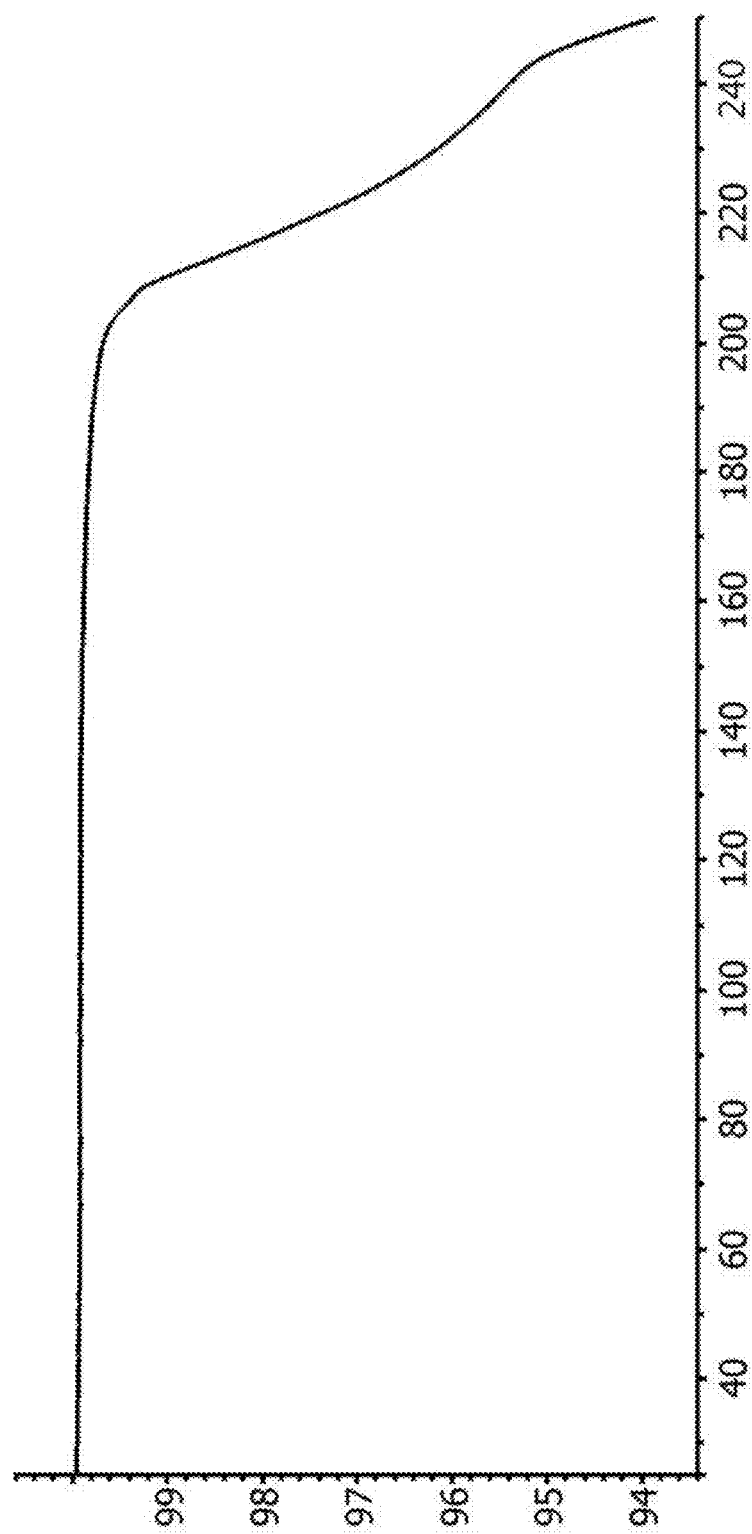
FIG. 5: illustrates a representative TGA curve of the the roxadustat L-proline co-crystal according to the present invention. The x-axis shows the temperature in degree Celsius (° C.), the y-axis shows the mass (loss) of the sample in weight percent (weight %).
Figure 6:
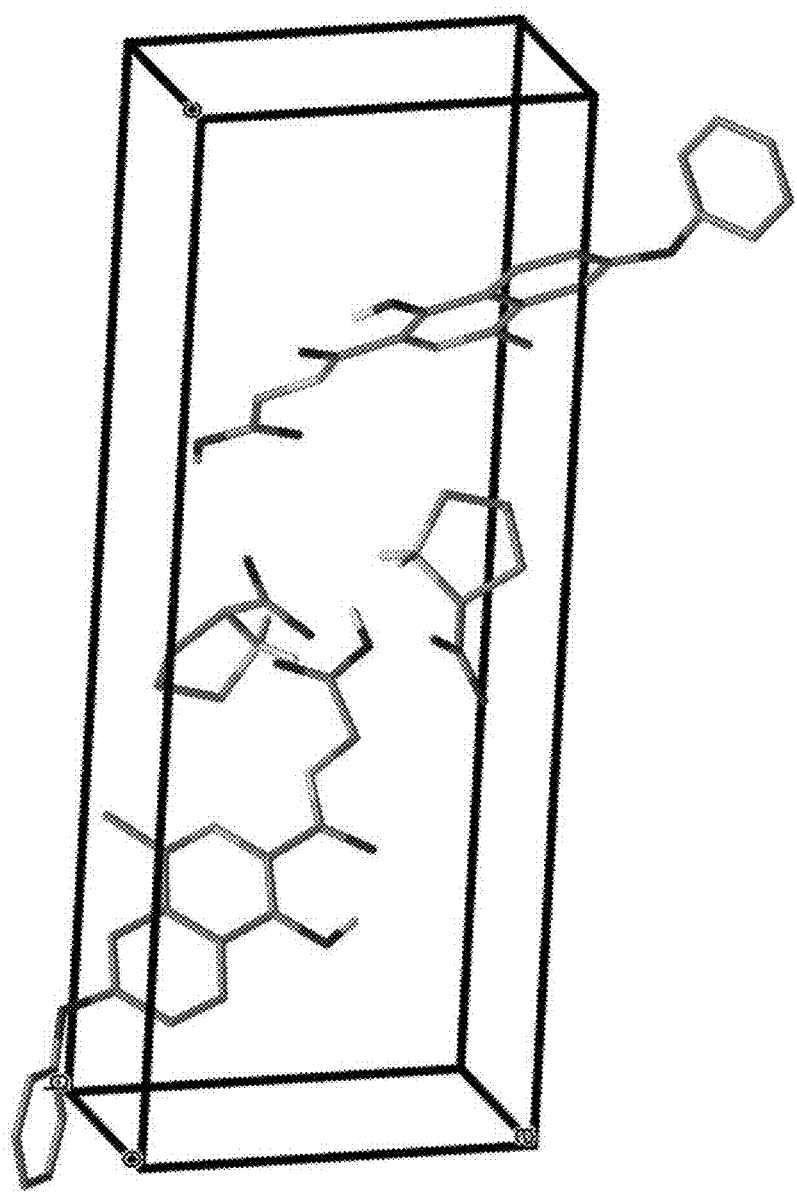
FIG. 6: illustrates the unit cell of the roxadustat L-proline co-crystal of the present invention.
Figure 8:
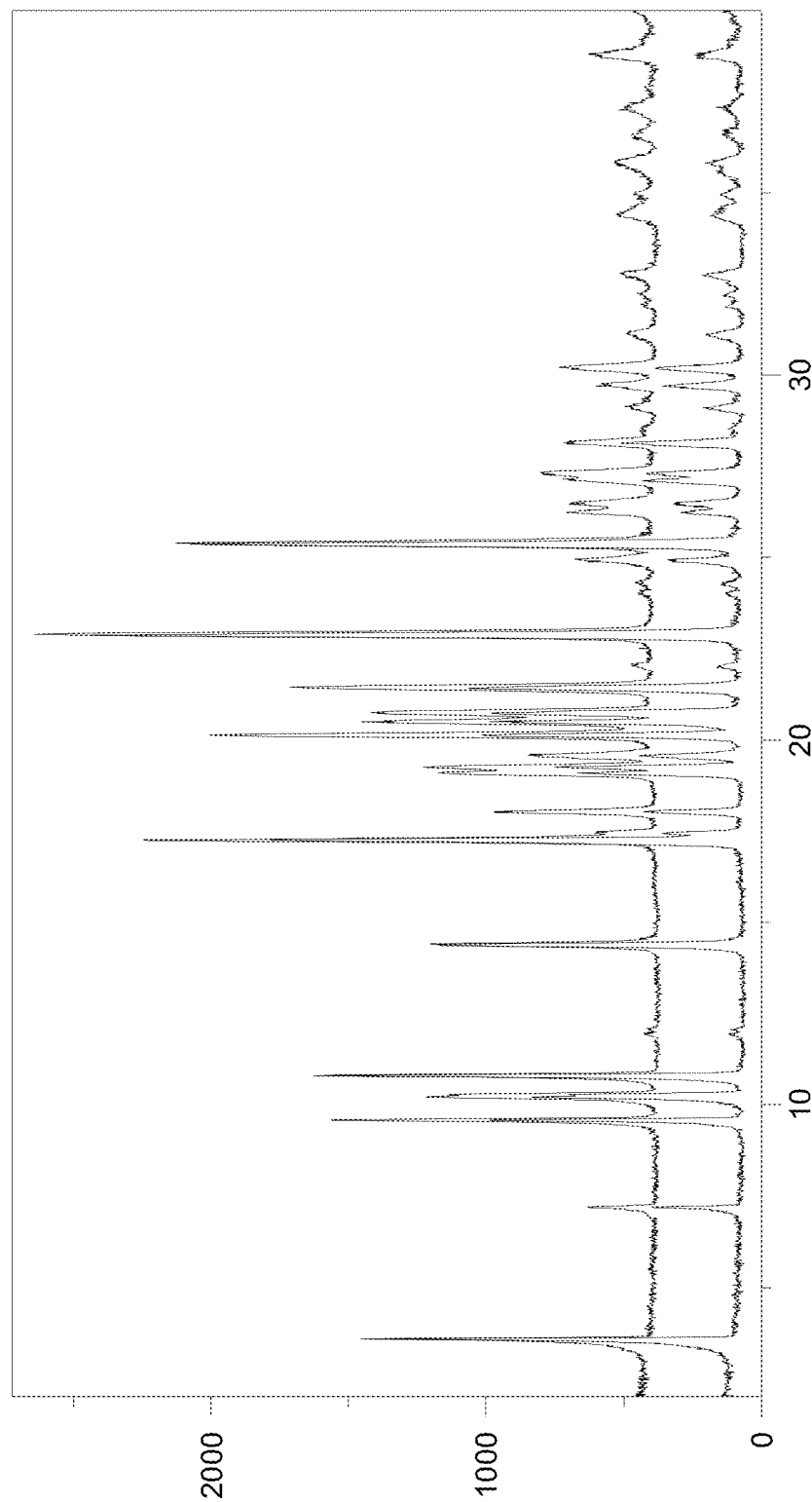
FIG. 8: illustrates a comparison of the PXRDs of the roxadustat L-proline co-crystal according to the present invention before (top) and after (bottom) subjecting the material to accelerated stress conditions of 40° C. and 75% RH for 7 days. The x-axis shows the scattering angle in ° 2-Theta, the y-axis shows the intensity of the scattered X-ray beam in counts of detected photons. The PXRD of the initial sample was shifted along the y-axis to separate the diffractograms for clarity reason.

Thermal analyses such as DSC and TGA revealed that the roxadustat L-proline co-crystal of the present invention is thermally highly stable e.g. does not undergo phase transformations or decomposition until it melts at about 206° C. This is in stark contrast to the hemihydrate form B as well as to the solvates form C and D disclosed in WO 2014/014835 A2, which show thermal events such as dehydration/desolvation and recrystallization events during DSC experiments, indicating solvent/water losses and phase transformations. It is worth mentioning that forms B, C and D all at least partially transform to form A during the DSC experiments, which is indicated by the final melting endotherm having a peak temperature of about 224° C., which can be assigned to the melting of form A (see FIGS. 4, 6 and 8 of WO 2014/014835 A2 and compare with FIG. 2).

In addition, according to the TGA curves provided in WO 2014/014835 A2 forms B, C and D readily lose their solvents/water upon heating.

Hence, the thermal stability of the roxadustat L-proline co-crystal of the present invention is superior compared to the hydrated/solvated forms B, C and D of WO 2014/014835 A2.

In another aspect, the present invention relates to a composition comprising the roxadustat L-proline co-crystal of the present invention as defined in any of the embodiments described above, said composition being essentially free of any other solid-state form of roxadustat. For example, a composition comprising the roxadustat L-proline co-crystal of the present invention comprises at most 20 weight %, preferably at most 10 weight %, more preferably at most 5 weight %, 4 weight %, 3 weight %, 2 weight % or 1 weight % of any other solid-state form of roxadustat, based on the weight of the composition. Preferably, the any other solid-state form of roxadustat is form A of WO 2014/014835 A2. Form A of roxadustat has a PXRD comprising amongst others characteristic reflections at 2-Theta angles of (8.5±0.2°) and (16.2±0.2°), when measured at a temperature in the range of from 20 to 30° C. with Cu-Kalpha$_{1,2}$ radiation having a wavelength of 0.15419 nm. Therefore, the absence of reflections at 2-Theta angles of (8.5±0.2°) and (16.2±0.2°) in the PXRD confirms the absence of roxadustat form A in the composition.

Hence, in a preferred embodiment, the present invention relates to a composition comprising the roxadustat L-proline co-crystal of the present invention as defined in any of the embodiments described above, said composition having a PXRD comprising no reflections at 2-Theta angles of (8.5±0.2°) and (16.2±0.2°), when measured at a temperature in the range of from 20 to 30° C. with Cu-Kalpha$_{1,2}$ radiation having a wavelength of 0.15419 nm.

In a further aspect, the present invention relates to a process for the preparation of the roxadustat L-proline co-crystal of the present invention or the composition comprising the roxadustat L-proline co-crystal as defined in any one of the aspects and their corresponding embodiments described above comprising:
(a) dissolving roxadustat together with L-proline in a solvent mixture comprising methanol and at least one cyclic ether;
(b) adding at least one aliphatic ether to the solution provided in (a);
(c) optionally, seeding the mixture obtained in (c) with roxadustat L-proline co-crystals according to the present invention;
(d) optionally, separating at least a part of the crystals obtained in (b) or (c) from the mother liquor;
(e) optionally, washing the isolated crystals obtained in (d); and
(f) optionally, drying the crystals obtained in any one of steps (b) to (e).

Roxadustat can for example be prepared according to the procedure provided in example 10 of WO 2014/014835 A2. Roxadustat may be applied as crystalline and/or amorphous material in step (a) of the above described procedure. Amorphous roxadustat may be prepared according to the procedures disclosed in example 6 of WO 2014/014835 A2. Suitable crystalline forms which may be used are for example forms A, B, C and D of WO 2014/014835 A2 (preparation of the forms see examples 1 to 4 of WO 2014/014835 A2), the dioxane solvate described herein (preparation see example 11 herein) or the acetic acid solvate described herein (preparation see example 12 herein). Preferably, the dioxane solvate described herein is used as starting material for the production of the roxadustat L-proline co-crystal of the present invention.

Roxadustat is dissolved in the solvent mixture at a concentration in the range of from about 20 to 30 g/L, most preferably the roxadustat concentration of the solution provided in (a) is 25 g/L. The molar ratio of roxadustat and L-proline applied is in the range of from 1.0:0.8 to 1.0 to 1.2, preferably of from 1.0:0.9 to 1.0 to 1.1, even more preferably of from 1.0 to 0.95 to 1.0 to 1.05 and most preferably the molar ratio is 1.0:1.0. The solvent mixture is preferably composed of methanol and at least one cyclic ether at a 1:1 volume ratio. Preferably, the at least one cyclic ether is selected from from THF and/or 1,4-dioxane. The solution may be prepared at RT or at elevated temperature, preferably the solution is prepared at RT.

In order to initiate crystallization of the roxadustat L-proline co-crystal, an antisolvent selected from at least one aliphatic ether is added in step (b) of the above described procedure. The aliphatic ether may be selected from the group consisting of diisopropyl ether, tert-butylmethyl ether and diethyl ether or any mixtures thereof. Preferably, diisopropyl ether and/or tert-butylmethyl ether are used. The volume ratio of the solvent mixture provided in step (a) and the antisolvent added in step (b) is in the range of from 1.0:0.5 to 1.0 to 1.5, preferably of from 1.0:0.5 to 1.0 to 1.0.

Optionally, roxadustat L-proline co-crystals may be added as seeds in order to promote crystallization and/or to control particle size distribution. The amount of seed crystals employed may range from about 1 to 20 weight %, preferably from about 1 to 10 weight % and most preferably from about 1 to 5 weight %, based on the weight of applied roxadustat starting material. Seed crystals may be prepared according to steps (a) to (b) of the above described procedure e.g. according to the procedure disclosed in example 2 of the present invention.

The obtained suspension may optionally be slurried, preferably at room temperature but slurrying may also be conducted at elevated temperature for example at a temperature in the range of from about 40 to 50° C. Slurrying encompasses any kind of movement of the solid material suspended in water caused by, but not limited to e.g. agitation, stirring, mixing, shaking, vibration, sonication, wet milling and the like.

Slurrying may be conducted for a time sufficient that at least a substantial part, preferably all of the roxadustat starting material has converted to the roxadustat L-proline co-crystal of the present invention. Preferably slurrying is performed for a period in the range of from several hours to several days. Slurrying may for example be performed for a period in the range of from 2 hours to 7 days. The skilled person may monitor the conversion of roxadustat to the roxadustat L-proline co-crystal of the present invention by withdrawing samples from the slurry and analyzing the samples by e.g. powder X-ray diffraction.

Once the roxadustat L-proline co-crystal of the present invention is obtained or preferably obtained in essentially pure form, at least a part of the crystals may be optionally separated from the mother liquor. Preferably, the crystals are separated from their mother liquor by any conventional method such as filtration, centrifugation, solvent evaporation or decantation, more preferably by filtration or centrifugation and most preferably by filtration.

Optionally, in a further step the isolated crystals are washed with at least one aliphatic ether selected from the group consisting of diisopropyl ether, tert-butylmethyl ether and diethyl ether or any mixtures thereof. Preferably, diisopropyl ether and/or tert-butylmethyl ether are used.

The obtained crystals may then optionally be dried. Drying may be performed at a temperature in the range of from about 20 to 80° C., preferably in the range of from about 20 to 40° C. and most preferably drying is performed at RT. Drying may be performed for a period in the range of from about 1 to 72 hours, preferably of from about 2 to 48 hours, more preferably of from about 4 to 24 hours and most preferably of from about 6 to 18 hours. Drying may be performed at ambient pressure and/or under reduced pressure. Preferably, drying is performed at a pressure of about 100 mbar or less, more preferably of about 50 mbar or less and most preferably of about 30 mbar or less, for example a vacuum of about 25 mbar is applied for drying.

In a further aspect, the present invention relates to the use of the roxadustat L-proline co-crystal of the present invention or the composition comprising the roxadustat L-proline co-crystal as defined in any one of the aspects and their corresponding embodiments described above for the preparation of a pharmaceutical composition.

In a further aspect, the present invention relates to a pharmaceutical composition comprising the roxadustat L-proline co-crystal of the present invention or the composition comprising the roxadustat L-proline co-crystal as defined in any one of the aspects and their corresponding embodiments described above, preferably in an effective and/or predetermined amount, and at least one pharmaceutically acceptable excipient. Optionally, the pharmaceutical composition further comprises at least one photostabilizing agent, preferably in an effective and/or predetermined amount.

Preferably, the predetermined and/or effective amount of the roxadustat L-proline co-crystal of the present invention is in the range of from 20 to 200 mg calculated as roxadustat. For example the predetermined and/or effective amount of the roxadustat L-proline co-crystal of the present invention is 20 mg, 50 mg, 100 mg, 150 mg or 200 mg, preferably 20 mg, 50 mg or 100 mg and most preferably 20 or 50 mg calculated as roxadustat.

The at least one pharmaceutically acceptable excipient, which is comprised in the pharmaceutical composition of the present invention, is preferably selected from the group consisting of fillers, diluents, binders, disintegrants, lubricants, glidants and combinations thereof. Preferably, the at least one pharmaceutically acceptable excipient is selected from the group consisting of lactose monohydrate, microcrystalline cellulose, povidone, croscarmellose sodium, magnesium stearate and combinations thereof. Even more preferably, all of these pharmaceutically acceptable excipients are comprised by the pharmaceutical composition of the present invention.

In another preferred embodiment, the at least one photostabilizing agent comprises titanium dioxide and at least one additional dye.

In one embodiment, the at least one additional dye blocks or reduces light at a wavelength range of from 100 to 800 nm, preferably of from 150 to 700 nm, more preferably of from 200 to 550 nm and most preferably of from 360 to 440 nm. In a further embodiment, the at least one additional dye is selected from the group consisting of a black dye, a blue dye, a green dye, a red dye, an orange dye, a purple dye, a violet dye, a yellow dye and combinations thereof, preferably from a red dye, an orange dye, a yellow dye and combinations thereof. In still a further embodiment, the at least one additional dye is selected from the group consisting of Caramel, iron oxide black, iron oxide red, iron oxide yellow, Allura Red AC, Allura Red AC aluminium lake, Carmine, Erythrosine, beta-carotene or mixtures of carotenes, Curcumin, Sunset Yellow FCF, Sunset Yellow FCF aluminium lake, Tartrazine, chlorophylls and chlorophyllins or Cu complexes thereof, Fast Green FCF, Brillant Blue FCF, Indigotine, Indigotine aluminium lake and combinations thereof. Preferably, the at least one additional dye is selected from the group consisting of Allura Red AC, Allura Red AC aluminium lake, iron oxide red, iron oxide yellow, Sunset Yellow FCF, Sunset Yellow FCF aluminium lake, Indigotine, Indigotine aluminium lake and combinations thereof.

In a particular embodiment, the at least one photostabilizing agent comprises titanium dioxide and Allura Red AC aluminium lake. In another embodiment, the at least one photostabilizing agent comprises titanium dioxide and iron oxide red. In another embodiment, the at least one photostabilizing agent comprises titanium dioxide, Allura Red AC and iron oxide yellow. In another embodiment, the at least one photostabilizing agent comprises titanium dioxide, iron oxide red, Allura Red AC and iron oxide yellow. In another embodiment, the at least one photostabilizing agent comprises titanium dioxide, iron oxide red and iron oxide yellow. In another embodiment, the at least one photostabilizing agent comprises titanium dioxide and iron oxide yellow.

Preferably, the pharmaceutical composition of the present invention as described above is an oral solid dosage form.

In a particular embodiment, the pharmaceutical composition of the present invention as describe above is a tablet, preferably a film-coated tablet comprising a tablet core and a coating.

The tablet or tablet core may be prepared by mixing the roxadustat L-proline co-crystal with at least one excipient such as fillers, diluents, binders, disintegrants, lubricants, glidants or combinations thereof and optionally with at least one photostabilizing agent followed by compressing the mixture. Optionally, a dry granulation step is performed before compression. Preferably, the tablet core is subsequently coated with a film-coat, whereat non-limiting examples of coatings include polyvinylalcohol-based, hydroxyethylcellulose, hydroxypropylmethylcellulose, carboxymethylcellulose sodium polyethylene glycol 4000 and cellulose acetate phthalate coatings. Methods of preparing such tablets, tablet cores and film-coated tablets are well known in the pharmaceutical arts.

The at least one photostabilizing agent of a film-coated tablet may be present in the tablet core and/or in the coating.

In another particular embodiment, the pharmaceutical composition of the present invention as describe above is a capsule. In a further embodiment, the capsule shell is a gelatin shell or a hydroxypropylmethylcellulose (HPMC) shell.

The at least one photostabilizing agent of the capsule may be present in the capsule fill and/or in the capsule shell.

In a further aspect, the present invention relates to the roxadustat L-proline co-crystal, the composition comprising the roxadustat L-proline co-crystal or the pharmaceutical composition comprising the roxadustat L-proline co-crystal as defined in any one of the above described aspects and their corresponding embodiments for use as a medicament.

In yet another aspect, the present invention relates to the roxadustat L-proline co-crystal, the composition comprising the roxadustat L-proline co-crystal or the pharmaceutical composition comprising the roxadustat L-proline co-crystal as defined in any one of the above described aspects and their corresponding embodiments for use in the treatment and/or prevention of anemia. For example, anemia is selected from the group consisting of iron deficiency anemia, sickle cell anemia, constitutional aplastic anemia, unspecified aplastic anemia, non-autoimmune haemolytic anemia, anemia complicating pregnancy, childbirth or the puerperium, pernicious anemia, nutritional anemia, autoimmune haemolytic anemia and anemia due to enzyme deficiency, congestive heart failure (CHF), chronic kidney disease (CKD), myelodysplastic syndrome, pregnancy, Crohn's disease, regional enteritis, inflammatory bowel disease (IBS), ulcerative colitis, ulcerative proctitis, idiopathic proctocolitis, myocardial infarction (MI), heart attack, systemic lupus erythematosus (SLE), agranulocytosis, cancer, end stage renal disease (ESRD), chronic obstructive pulmonary disease (COPD), rheumatoid arthritis (RA), acute renal failure (ARF), pneumonia and pulmonary artery hypertension.

In a particular preferred embodiment, the invention relates to the roxadustat L-proline co-crystal, the composition comprising the roxadustat L-proline co-crystal or the pharmaceutical composition comprising the roxadustat L-proline co-crystal as defined in any one of the above described aspects and their corresponding embodiments for use in the treatment and/or prophylaxis of anemia in patients with end-stage renal disease (ESRD) and/or chronic kidney disease (CKD). Even more preferably, patients include both dialysis dependent and non-dialysis dependent patients.

In another preferred embodiment, the invention concerns a method of treating and/or preventing anemia, said method comprising administering an effective amount of the roxadustat L-proline co-crystal as defined in the above described aspect and its corresponding embodiments to a patient in need of such a treatment.

In yet another preferred embodiment, the invention concerns a method of treating and/or preventing anemia in patients with end-stage renal disease (ESRD) and/or chronic kidney disease (CKD), said method comprising administering an effective amount of the roxadustat L-proline co-crystal as defined in the above described aspect and its corresponding embodiments to a patient in need of such a treatment.

In still another preferred embodiment, the invention concerns a method of treating and/or preventing anemia in patients with end-stage renal disease (ESRD) and/or chronic kidney disease (CKD), including patients who are both dialysis dependent and non-dialysis dependent, said method comprising administering an effective amount of the roxadustat L-proline co-crystal as defined in the above described aspect and its corresponding embodiments to a patient in need of such a treatment.

In yet another aspect the present invention relates to a container comprising a pharmaceutical composition comprising the roxadustat L-proline co-crystal of the present invention as defined in any one of the aspects and their corresponding embodiments described above, preferably a pharmaceutical composition wherein the roxadustat L-proline co-crystal of the present invention is present in an effective and/or predetermined amount. Preferably the pharmaceutical composition comprising the roxadustat L-proline co-crystal which is packaged in said container is a tablet or a capsule.

The container can be a packaging for bulk shipment, such as fiber drums with plastic liners, bulk boxes or other shipping containers. However, preferably the container is a packaging useful for the packaging of pharmaceutical compositions intended for the patient, such as a blister packaging or a glass bottle or a plastic bottle. It is preferred that the packaging comprises a packaging material, wherein said packaging material is capable of blocking, absorbing, and/or reflecting light at a wavelength range of from 100 to 550 nm, and preferably of from 360 to 440 nm, in order to provide additional light protection during shipping and storage. For example, the packaging material may consist of aluminum foil (Alu/Alu blister) or may be a blister comprising aluminum foil and/or polyvinyl chloride (PVC) or polyvinylidene chloride (PVDC) correspondingly selected to block, absorb and/or reflect UV exposure up to a wavelength of 450 nm, or, as another example, may be made of a combined aluminum/polymer foil.

EXAMPLES

The following non-limiting examples are illustrative for the disclosure and are not to be construed as to be in any way limiting for the scope of the invention.

Example 1: Preparation of the Roxadustat L-Proline Co-Crystal of the Present Invention Roxadustat (2.0 g, e.g. prepared according to the method disclosed in example 10 of WO 2014/014835 A2) and L-proline (690 mg, commercial sample from Sigma Aldrich) were dissolved at room temperature in a mixture of methanol (40 mL) and THF (40 mL). Diisopropyl ether (40 mL) and seed crystals (20 mg, roxadustat L-proline co-crystals prepared according to example 2 herein) were added to the solution consecutively in order to initiate crystallization. The obtained suspension was stirred for 2 hours before the obtained crystals were collected by filtration and dried at room temperature under vacuum (25 mbar) to obtain 1.8 g (yield: 67% of theory) of the roxadustat L-proline co-crystal according to the present invention.

Example 2: Preparation of Roxadustat L-Proline Co-Crystal Seed Crystals

Roxadustat (100 mg, e.g. prepared according to the method disclosed in example 10 of WO 2014/014835 A2) and L-proline (34.5 mg, commercial sample from Sigma Aldrich) were dissolved at room temperature in a mixture of methanol (2 mL) and 1,4-dioxane (2 mL). Diisopropyl ether (5 mL) was added and the solution was allowed to stand in the refrigerator at about 2-8° C. for 16 hours in order to initiate crystallization. The obtained crystals were collected by filtration and dried at room temperature under vacuum (25 mbar) to obtain the roxadustat L-proline co-crystal according to the present invention.

Example 3: Powder X-Ray Diffraction

The roxadustat L-proline co-crystal according to the present invention was investigated by powder X-ray diffraction, which was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-theta with 40 s per step (255 channels) in the angular range of 2° to 40° 2-Theta at ambient conditions. A typical precision of the 2-Theta values is in the range of ±0.2° 2-Theta, preferably of ±0.1° 2-Theta. Thus, the diffraction peak of the roxadustat L-proline co-crystal of the present invention at 3.6° 2-Theta can appear in the range of from 3.4 to 3.8° 2-Theta, preferably in the range of from 3.5 to 3.7° 2-Theta on most X-ray diffractometers under standard conditions.

A representative diffractogram of the roxadustat L-proline co-crystal according to the present invention is displayed in FIG. 1 and the corresponding reflection list (peak list) from 2 to 30° 2-Theta is provided in table 1 below.

TABLE 1

Reflection (peak) positions of the roxadustat L-proline co-crystal according to the present invention in the range of from 2 to 30° 2-Theta; A typical precision of the 2-Theta values is in the range of ±0.2° 2-Theta, preferably of ±0.1° 2-Theta.
Reflection position [° 2-Theta]

| |
|---|
| 3.6 |
| 7.2 |
| 9.6 |
| 10.2 |
| 10.3 |
| 10.8 |
| 11.9 |
| 12.1 |
| 14.4 |
| 17.3 |
| 17.5 |
| 18.0 |
| 19.1 |
| 19.3 |
| 19.6 |
| 20.1 |
| 20.5 |
| 20.8 |
| 21.4 |
| 22.0 |
| 22.9 |
| 24.0 |
| 24.3 |
| 24.9 |
| 25.4 |
| 26.2 |
| 26.5 |
| 27.1 |
| 27.3 |
| 28.1 |
| 29.1 |
| 29.7 |

Example 4: Fourier Transform Infrared Spectroscopy

The roxadustat L-proline co-crystal according to the present invention was investigated by FTIR spectroscopy. The FTIR spectrum was recorded (obtained) on a MKII Golden Gate™ Single Reflection Diamond ATR cell with a Bruker Tensor 27 FTIR spectrometer with 4 cm$^{-1}$ resolution at RT. To record a spectrum a spatula tip of the sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of from about ±2 cm$^{-1}$. Thus, the infrared peak of the roxadustat L-proline co-crystal according to the present invention at 3379 cm$^{-1}$ can appear between 3377 and 3381 cm$^{-1}$ on most infrared spectrometers under standard conditions.

A representative FTIR spectrum of the roxadustat L-proline co-crystal according to the present invention is displayed in FIG. 2 and the corresponding peak list is provided in table 2 below.

TABLE 2

FTIR peak list of the roxadustat L-proline co-crystal according to the present invention; a typical precision of the wavenumbers is in the range of ±2 cm$^{-1}$.
Wavenumber [cm$^{-1}$]

| |
|---|
| 3379 |
| 3071 |
| 1705 |
| 1624 |
| 1529 |
| 1487 |
| 1408 |
| 1332 |
| 1244 |
| 1203 |
| 941 |
| 889 |
| 801 |
| 770 |
| 719 |
| 689 |
| 651 |

Example 5: Raman Spectroscopy

The roxadustat L-proline co-crystal according to the present invention was investigated by Raman spectroscopy. The Raman spectrum was recorded with a BRUKER Senterra Raman spectrometer microscope at room temperature using a 785 nm laser. The sample was brought to focus with a 20× long working distance objective. Then spectra were collected at 9 to 12 cm$^{-1}$ resolution. A typical precision of the wavenumber values is in the range of from ±1 to ±3 cm$^{-1}$. Thus, the peak of the roxadustat L-proline co-crystal of the present invention at 1629 cm$^{-1}$ can appear between 1626 and 1632 cm$^{-1}$, preferably between 1628 and 1630 cm$^{-1}$ on most Raman spectrometers under standard conditions.

A representative Raman spectrum of the roxadustat L-proline co-crystal according to the present invention is displayed in FIG. 3 and the corresponding peak list is provided in table 3 below.

TABLE 3

Raman peak list of the roxadustat L-proline co-crystal according to the present invention; a typical precision of the wavenumbers is in the range of from ±1 to ±3 cm$^{-1}$.
Wavenumber [cm$^{-1}$]

| |
|---|
| 1629 |
| 1583 |
| 1536 |
| 1506 |
| 1455 |
| 1412 |
| 1366 |
| 1341 |
| 1296 |
| 1186 |
| 1100 |

TABLE 3-continued

Raman peak list of the roxadustat L-proline co-crystal according to the present invention; a typical precision of the wavenumbers is in the range of from ±1 to ±3 cm$^{-1}$.

| Wavenumber [cm$^{-1}$] |
| --- |
| 1003 |
| 963 |
| 908 |
| 821 |
| 721 |
| 621 |
| 518 |
| 486 |
| 346 |
| 285 |
| 227 |

Example 6: Single Crystal X-Ray Diffraction

Intensity data for the crystal structure of the roxadustat L-proline co-crystal of the present invention were collected with Mo (lambda=0.71073 Angstrom) radiation on an Oxford Diffraction Gemini-R Ultra diffractometer at 173 K. The structure was solved using the direct methods procedure in SHELXT and refined by full-matrix least squares on F$^2$ using SHELXL-2014. All H atoms were located in difference maps. H atoms bonded to O or N atoms were refined with restrained distances [O–H=0.84 Å; N–H=0.88 Å) and their U$_{iso}$ parameters were refined freely. The H atoms bonded to C atoms were refined using a riding model with U$_{iso}$ set at 1.2U$_{eq}$ or 1.5U$_{eq}$ of the parent C atom.

Example 7: Differential Scanning Calorimetry (DSC)

The roxadustat L-proline co-crystal according to the present invention was investigated by DSC, which was performed on a Mettler Polymer DSC R instrument. The sample (2.72 mg) was heated in a 40 microliter aluminium pan with a pierced aluminium lid from 25 to 250° C. at a rate of 10 K/min. Nitrogen (purge rate 50 mL/min) was used as purge gas.

The DSC curve shows a single endothermic peak with an onset temperature of about 206° C. and a peak temperature of about 207° C., which is due to the melting of the sample. The anhydrous and non-solvated nature of the co-crystal and its excellent thermal stability are evidenced by the fact that neither phase changes nor desolvation events are detectable until the sample melts.

Example 8: Thermogravimetric Analysis (TGA)

The roxadustat L-proline co-crystal according to the present invention was investigated by TGA, which was performed on a Mettler TGA/DSC 1 instrument. The sample (16.28 mg) was heated in a 100 microliter aluminum pan closed with an aluminum lid. The lid was automatically pierced at the beginning of the measurement. The sample was heated from 25 to 250° C. at a rate of 10 K/min. Nitrogen (purge rate 50 mL/min) was used as purge gas.

The TGA curve shows no significant mass loss until the sample melts. For example mass losses of only about 0.1 weight % up to a temperature of about 180° C., about 0.2 weight % up to a temperature of about 190° C. and about 0.3 weight % up to a temperature of about 200° C. were observed, which further proves the presence of an anhydrous and non-solvated co-crystal.

Example 9: Physical Stability of the Roxadustat L-Proline Co-Crystal of the Present Invention

Example 9.1: Stability Against Temperature and Moisture

The roxadustat L-proline co-crystal of the present invention was subjected to an atmosphere having a temperature of 40° C. and a relative humidity of 75% for 7 days. According to powder X-ray diffraction no phase changes occurred during this period (see FIG. 8 herein).

Example 9.2: Stability Against Pressure

Figure 9:
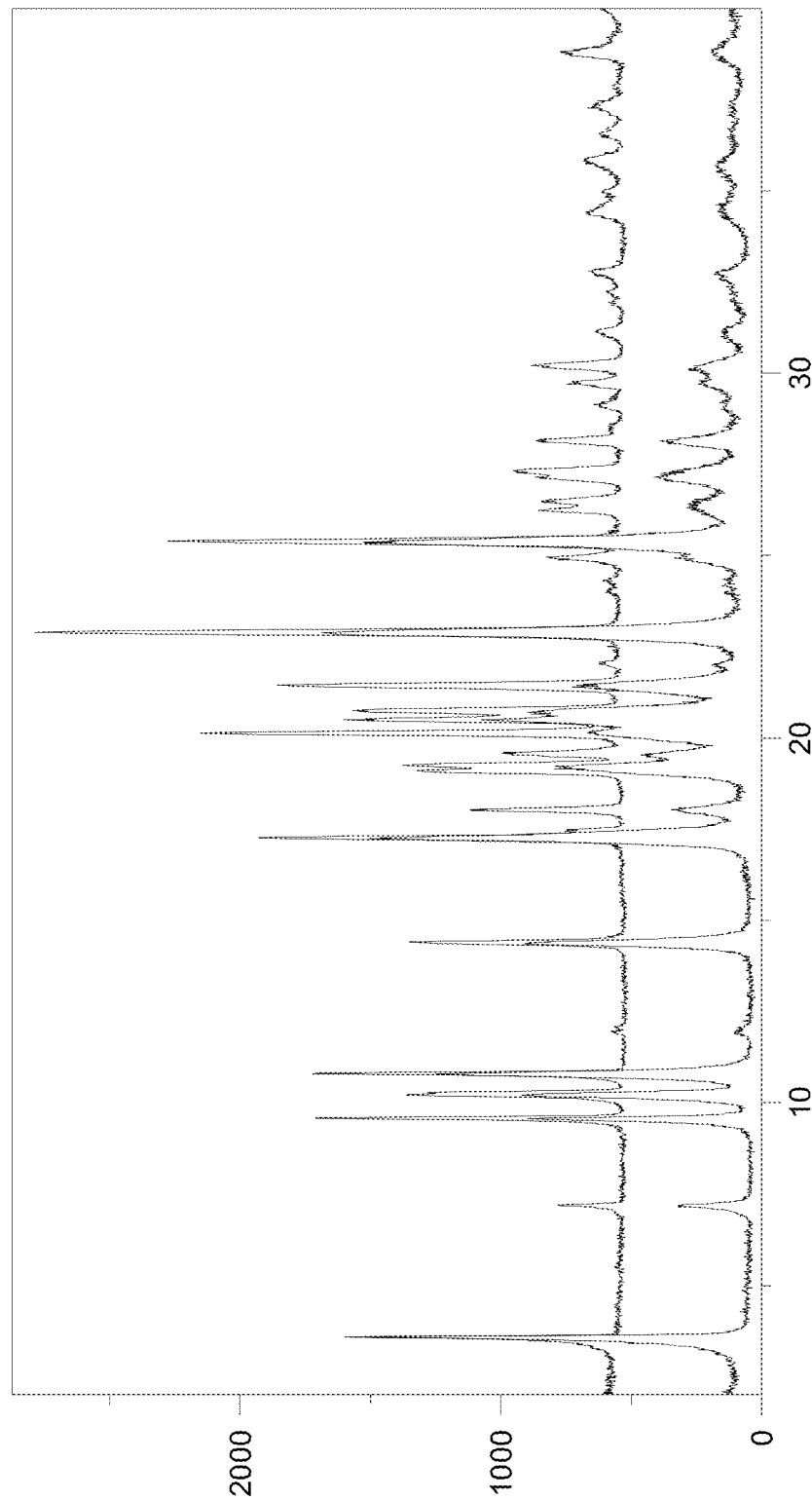
FIG. 9: illustrates a comparison of the PXRDs of the roxadustat L-proline co-crystal according to the present invention before (top) and after (bottom) subjecting the material to a pressure of about 100 kN. The x-axis shows the scattering angle in ° 2-Theta, the y-axis shows the intensity of the scattered X-ray beam in counts of detected photons. The PXRD of the initial sample was shifted along the y-axis to separate the diffractograms for clarity reason.

The roxadustat L-proline co-crystal of the present invention was pressed to a pellet using an IR press at a pressure of about 100 kN. The pellet was ground again in order to obtain a powder, which was then investigated by PXRD. According to powder X-ray diffraction no phase changes occured (see FIG. 9 herein).

Example 9.3: Stability Against Mechanical Stress

Figure 10:
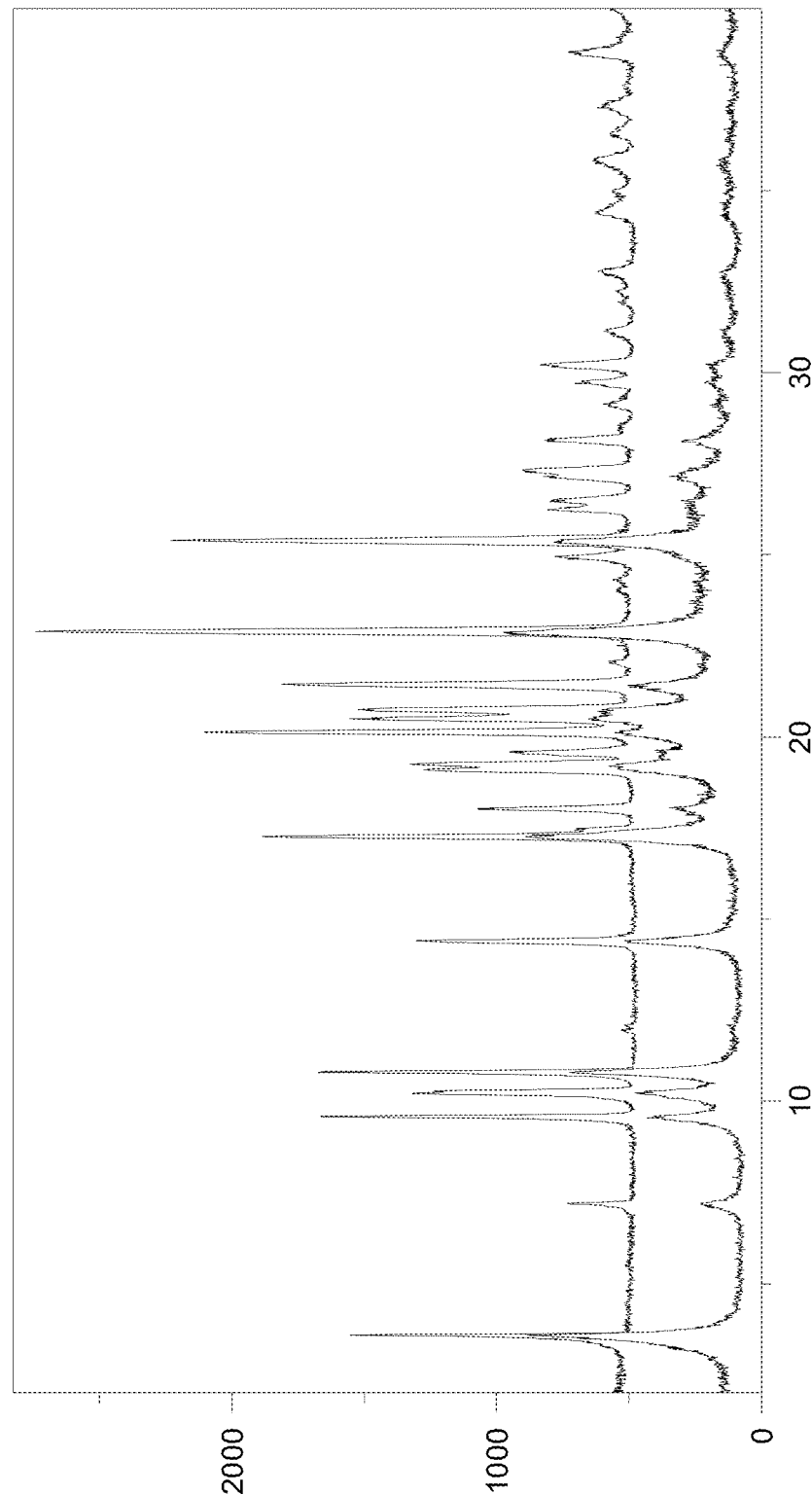
FIG. 10: illustrates a comparison of the PXRDs of the roxadustat L-proline co-crystal according to the present invention before (top) and after (bottom) milling. The x-axis shows the scattering angle in ° 2-Theta, the y-axis shows the intensity of the scattered X-ray beam in counts of detected photons. The PXRD of the initial sample was shifted along the y-axis to separate the diffractograms for clarity reason.

The roxadustat L-proline co-crystal of the present invention was dry ground using a Retsch mixer mill MM 301. A 1.5 mL grinding jar with one ball (5 mm diameter) both made of stainless steel was fed with about 70 mg sample and ground for 20 minutes at a frequency of 25 vibrations per second. According to powder X-ray diffraction no phase changes occured (see FIG. 10 herein).

Example 10: Dissolution rate in phosphate buffer pH 6 at 25° C.

Figure 7:
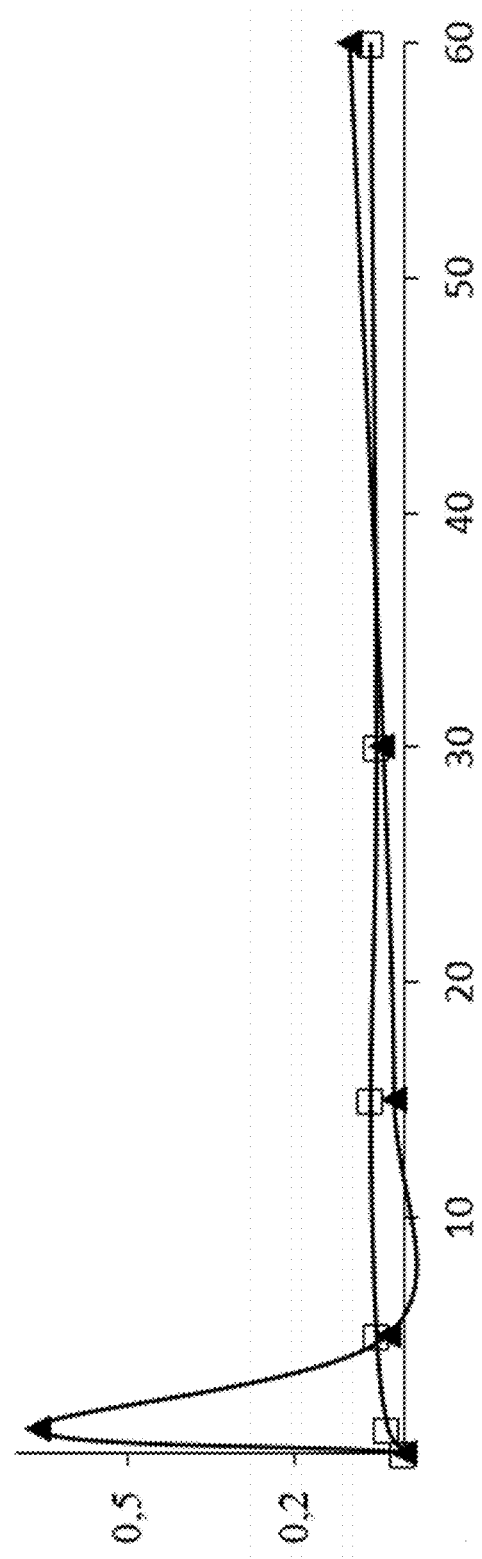
FIG. 7: displays the dissolution curves of the roxadustat L-proline co-crystal of the present invention (black triangles) and roxadustat form A of WO 2014/014835 A2 (white squares) in phosphate buffer pH 6 measured at 25° C. The x-axis shows the time in minutes, the y-axis the roxadustat concentration of the solution in g/L.

Powder dissolution experiments were carried out in phosphate buffer pH 6 at 25° C. for form A of roxadustat and the L-proline co-crystal of the present invention. The respective concentrations were determined by HPLC at a wavelength of 254 nm. As can be seen from table 4 and FIG. 7 herein the roxadustat L-proline co-crystal exhibited an approximately twentyfold increase in aqueous solubility after 1 minute compared to form A. The complex formed between L-proline and roxadustat falls apart in aqueous solution to generate its pure components after only about 5 minutes.

TABLE 4

Dissolution profile of roxadustat form A of WO 2014/014835 A2 and the roxadustat L-proline co-crystal of the present invention in phosphate buffer pH 6. The corresponding graphs are displayed in FIG. 7 herein.

| time [min] | Concentration roxadustat form A | Concentration roxadustat L-prolin co-crystal |
| --- | --- | --- |
| 1 min | 0.03 g/L | 0.66 g/L |
| 5 min | 0.05 g/L | 0.03 g/L |
| 15 min | 0.06 g/L | 0.02 g/L |
| 30 min | 0.05 g/L | 0.04 g/L |
| 60 min | 0.06 g/L | 0.10 g/L |
| 180 min | 0.07 g/L | 0.09 g/L |

Example 11: Preparation of the Roxadustat Dioxane Solvate

Roxadustat (1.0 g, e.g. prepared according to the method disclosed in example 10 of WO 2014/014835 A2) was dissolved in 1,4-dioxane (7 mL) upon heating. The obtained clear solution was cooled to RT and stored in a refrigerator at about 2-8° C. for 68 hours in order to initiate crystallization. The obtained crystals were collected by filtration and sucked dry on the filter in order to obtain 0.75 g of the roxadustat dioxane solvate.

Figure 11:
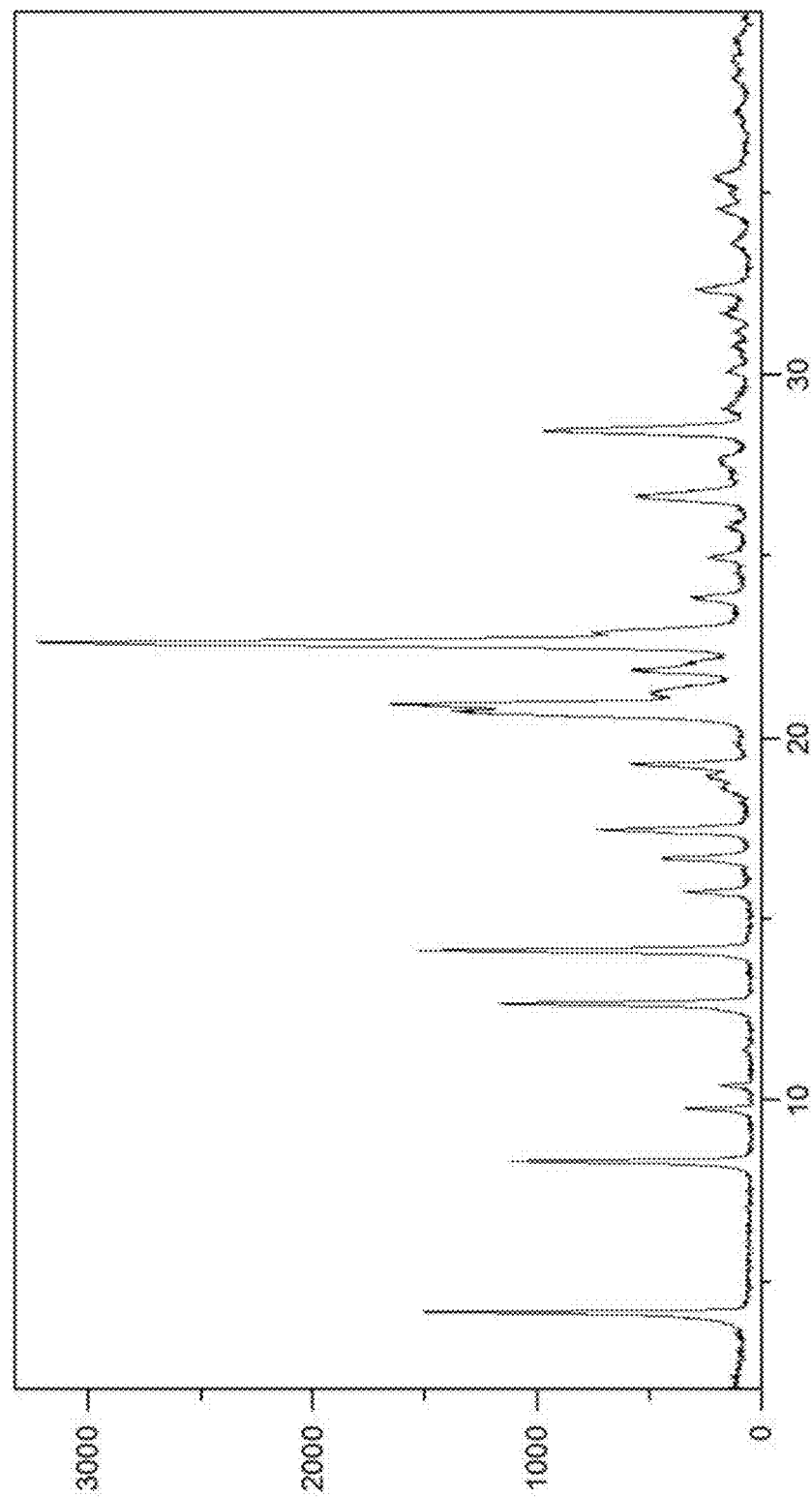
FIG. 11: illustrates a PXRD of the roxadustat 1,4-dioxane solvate prepared according to example 11 herein. The x-axis shows the scattering angle in ° 2-Theta, the y-axis shows the intensity of the scattered X-ray beam in counts of detected photons.

The roxadustat dioxane solvate was investigated by powder X-ray diffraction applying the experimental conditions as outlined in example 3 herein. A representative diffractogram of the roxadustat dioxane solvate is displayed in FIG. 11 and the corresponding reflection list (peak list) from 2 to 30° 2-Theta is provided in table 5 below.

TABLE 5

Reflection (peak) positions of the roxadustat dioxane solvate in the range of from 2 to 30° 2-Theta; A typical precision of the 2-Theta values is in the range of ±0.2° 2-Theta, preferably of ±0.1° 2-Theta.
Reflection position [° 2-Theta]

| |
|---|
| 4.1 |
| 8.3 |
| 9.8 |
| 10.4 |
| 11.4 |
| 12.7 |
| 14.1 |
| 15.7 |
| 16.6 |
| 17.4 |
| 18.6 |
| 18.9 |
| 19.3 |
| 20.7 |
| 20.9 |
| 21.2 |
| 21.8 |
| 22.6 |
| 22.9 |
| 23.8 |
| 25.0 |
| 25.8 |
| 26.6 |
| 27.6 |
| 28.4 |
| 29.1 |

Example 12: Preparation of the Roxadustat Acetic Acid Solvate

Roxadustat (1.0 g, e.g. prepared according to the method disclosed in example 10 of WO 2014/014835 A2) was dissolved in glacial acetic acid (20 mL) upon heating. The obtained clear solution was stored in a refrigerator at about 2-8° C. for 68 hours in order to initiate crystallization. After warming the suspension to RT the crystals were collected by filtration and dried at room temperature under vacuum (25 mbar) to obtain 0.8 g of the acetic acid solvate.

Figure 12:
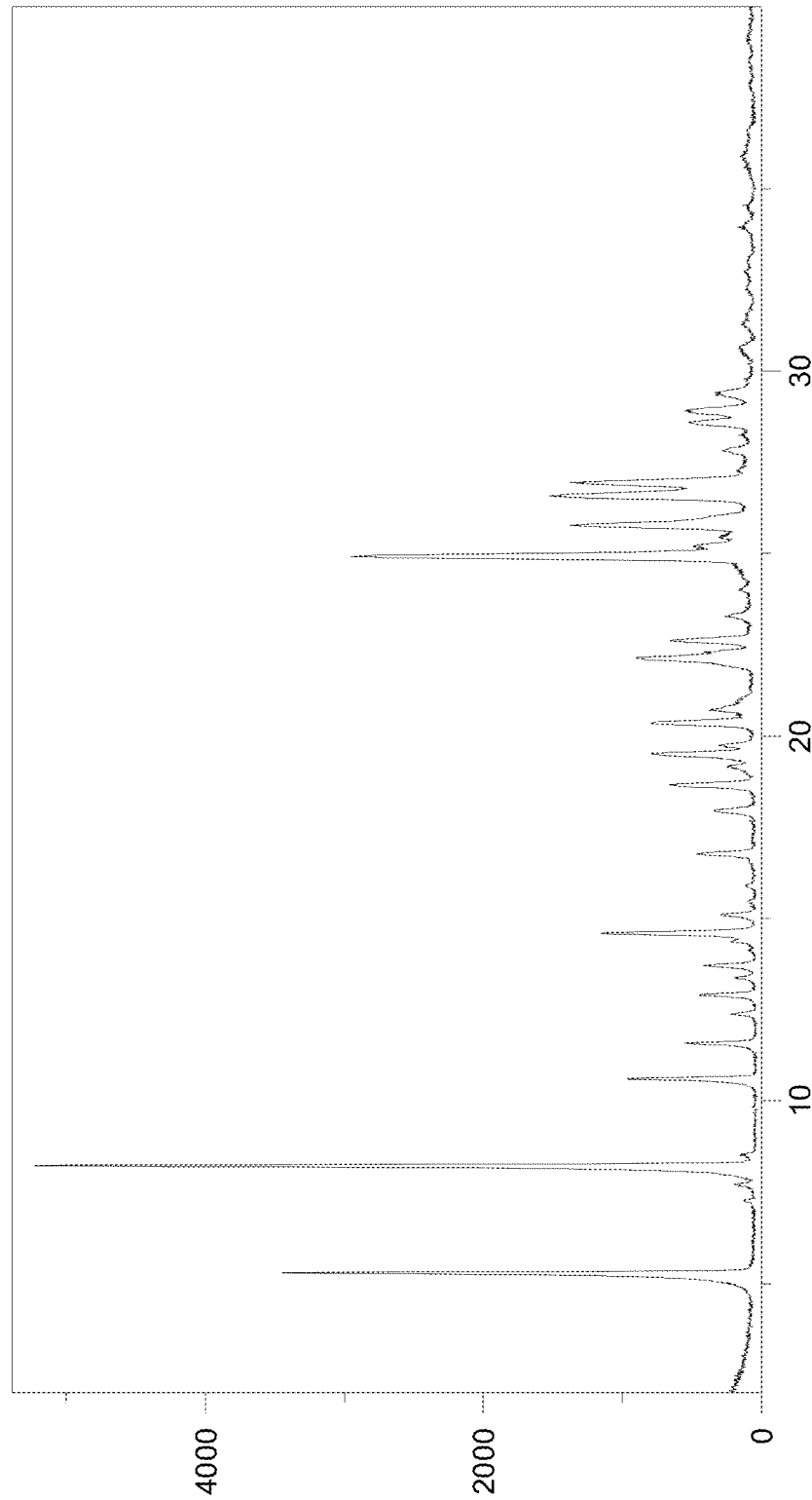
FIG. 12: illustrates a PXRD of the roxadustat acetic acid solvate prepared according to example 12 herein. The x-axis shows the scattering angle in ° 2-Theta, the y-axis shows the intensity of the scattered X-ray beam in counts of detected photons.

The roxadustat acetic acid solvate was investigated by powder X-ray diffraction applying the experimental conditions as outlined in example 3 herein. A representative diffractogram of the roxadustat acetic acid solvate is displayed in FIG. 12 and the corresponding reflection list (peak list) from 2 to 30° 2-Theta is provided in table 6 below.

TABLE 6

Reflection (peak) positions of the roxadustat acetic acid solvate in the range of from 2 to 30° 2-Theta; A typical precision of the 2-Theta values is in the range of ±0.2° 2-Theta, preferably of ±0.1° 2-Theta.
Reflection position [° 2-Theta]

| |
|---|
| 5.3 |
| 7.3 |
| 7.7 |

TABLE 6-continued

Reflection (peak) positions of the roxadustat acetic acid solvate in the range of from 2 to 30° 2-Theta; A typical precision of the 2-Theta values is in the range of ±0.2° 2-Theta, preferably of ±0.1° 2-Theta.
Reflection position [° 2-Theta]

| |
|---|
| 8.2 |
| 8.5 |
| 10.6 |
| 11.6 |
| 12.4 |
| 12.9 |
| 13.4 |
| 13.7 |
| 14.4 |
| 14.6 |
| 15.1 |
| 15.5 |
| 15.9 |
| 16.8 |
| 18.0 |
| 18.7 |
| 19.2 |
| 19.5 |
| 19.8 |
| 20.4 |
| 20.7 |
| 22.1 |
| 22.6 |
| 23.3 |
| 24.0 |
| 24.9 |
| 25.2 |
| 25.8 |
| 26.5 |
| 26.6 |
| 26.9 |
| 27.8 |
| 28.6 |
| 28.9 |
| 29.4 |

The invention claimed is:

1. A co-crystal of roxadustat with L-proline, wherein the co-crystal is characterized by having a powder X-ray diffractogram comprising reflections at 2-Theta angles of (3.6 ±0.2°), (7.2 ±0.2°) and (9.6 ±0.2°), when measured at a temperature in the range of from 20 to 30° C. with Cu-Kalpha$_{1,2}$ radiation having a wavelength of 0.15419 nm.

2. The co-crystal of claim 1 characterized by having the chemical structure according to formula B1 formula B1

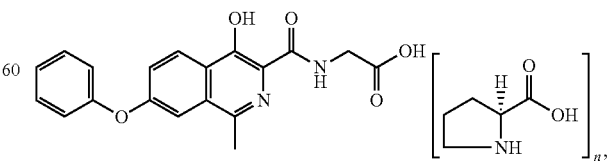

3. The co-crystal of claim 1 characterized by having the chemical structure according to formula B2 formula B2

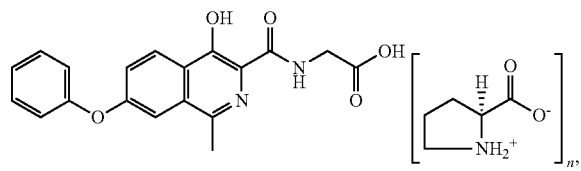

wherein n is in the range of from 0.9 to 1.1.

4. The co-crystal according to claim 1 characterized by having a Fourier transform infrared spectrum comprising peaks at wavenumbers of (3379 ±2) cm$^{-1}$, (3071±2) cm$^{-1}$ and (1705±2) cm$^{-1}$, when measured at a temperature in the range of from 20 to 30° C. with a diamond attenuated total reflection cell.

5. The co-crystal according to claim 1 characterized by having a Raman spectrum comprising peaks at wavenumbers of (1629±3) cm$^{-1}$, (1536±3) cm$^{-1}$ and (1412±3) cm$^{-1}$, when measured at a temperature in the range of from 20 to 30° C. and a wavelength of 785 nm.

6. A composition comprising the co-crystal as defined in claim 1 characterized by having a powder X-ray diffractogram comprising no reflections at 2-Theta angles of (8.5±0.2°) and (16.2±0.2°), when measured at a temperature in the range of from 20 to 30° C. with Cu-Kalpha$_{1,2}$ radiation having a wavelength of 0.15419 nm.

7. A pharmaceutical composition comprising the co-crystal as defined in claim 1 and at least one pharmaceutically acceptable excipient.

8. The pharmaceutical composition according to claim 7, wherein the pharmaceutical composition is an oral solid dosage form.

9. The pharmaceutical composition of claim 8, wherein the oral solid dosage form is a tablet or a capsule.

\* \* \* \* \*